(12) United States Patent
Nathan et al.

(10) Patent No.: US 11,633,508 B2
(45) Date of Patent: Apr. 25, 2023

(54) DEVICE FOR INCREASED ULTRAVIOLET EXPOSURE OF FLUIDS

(71) Applicant: VIOLET DEFENSE GROUP, INC., Orlando, FL (US)

(72) Inventors: Mark Nathan, Harmony, FL (US); Theresa Nathan, Harmony, FL (US)

(73) Assignee: VIOLET DEFENSE GROUP, INC., Orlando, FL (US)

(*) Notice: Subject to any disclaimer, the term of this patent is extended or adjusted under 35 U.S.C. 154(b) by 0 days.

(21) Appl. No.: 16/040,436

(22) Filed: Jul. 19, 2018

(65) Prior Publication Data
US 2018/0344885 A1    Dec. 6, 2018

Related U.S. Application Data

(63) Continuation-in-part of application No. 15/437,199, filed on Feb. 20, 2017, now Pat. No. 10,046,075, (Continued)

(51) Int. Cl.
*A61L 2/10* (2006.01)
*A61L 2/00* (2006.01)
*A61L 9/20* (2006.01)

(52) U.S. Cl.
CPC .............. *A61L 2/10* (2013.01); *A61L 2/0047* (2013.01); *A61L 9/20* (2013.01); *A61L 2202/14* (2013.01)

(58) Field of Classification Search
CPC ............. A47K 13/24; C02F 2201/3225; C02F 2201/328; A61L 2/10; A61L 2/0047; A61L 2202/14; A61L 9/20
See application file for complete search history.

(56) References Cited

U.S. PATENT DOCUMENTS 3,314,746 A    4/1967   Millar
4,710,634 A   12/1987   Brookes
(Continued)

FOREIGN PATENT DOCUMENTS

CN    102400491 A      4/2012
CN    204050421    * 12/2014   ............... A61L 9/20
(Continued)

OTHER PUBLICATIONS

European Office Action issued in EP 13855084.3 dated Oct. 9, 2018, 8 pages.
(Continued)

*Primary Examiner* — Sean M Luck
(74) *Attorney, Agent, or Firm* — Foley & Lardner LLP

(57) ABSTRACT

A device for increased ultraviolet exposure of fluids. The device includes at least one photonic source for generating and emitting photonic energy in a wavelength or in a range of wavelengths of visible light. The device also includes a lens formed of a fluoropolymer material wherein the at least one photonic source is sealed within an interior and underneath an outer surface of the fluoropolymer material so as to be surrounded by the fluoropolymer material. The at least one photonic source is coupled with the lens such that the photonic energy emitting from the at least one photonic source transmits through and projects beyond the fluoropolymer material. The lens propagates photons in an omnidirectional pattern simultaneously throughout the entirety of the lens. The joining of the at least one photonic source and the fluoropolymer material comprises all components for generating and emitting photonic energy when the photonic source is activated, such that it is an operable source. The operable source is submerged within a containment vessel which holds the fluids to be sanitized by the operable source. The fluid within the system are exposed to the photonic (Continued)

energy within the device for an extended period of time to effectively destroy pathogens and sanitize the target fluids.

27 Claims, 12 Drawing Sheets

Related U.S. Application Data which is a continuation of application No. 14/627,892, filed on Feb. 20, 2015, now Pat. No. 9,572,902, which is a continuation of application No. 14/078,288, filed on Nov. 12, 2013, now Pat. No. 8,993,988.

(60) Provisional application No. 61/796,521, filed on Nov. 13, 2012.

(56) References Cited

U.S. PATENT DOCUMENTS

| | | | |
|---|---|---|---|
| 4,819,276 A | 4/1989 | Stevens | |
| 4,968,437 A * | 11/1990 | Noll | A61L 2/10 210/223 |
| 5,008,933 A | 4/1991 | Kao et al. | |
| 5,230,792 A * | 7/1993 | Sauska | A61L 2/10 210/143 |
| 5,393,419 A * | 2/1995 | Tiede | A61L 2/10 210/192 |
| 5,611,089 A | 3/1997 | Cretors | |
| 5,813,752 A | 9/1998 | Singer et al. | |
| 5,813,753 A | 9/1998 | Vriens et al. | |
| 6,076,197 A | 6/2000 | Yeung | |
| 6,083,387 A * | 7/2000 | LeBlanc | A23L 2/50 210/199 |
| 6,099,799 A * | 8/2000 | Anderson | A61L 2/10 210/256 |
| 6,139,803 A | 10/2000 | Watanabe et al. | |
| 6,193,894 B1 | 2/2001 | Hollander | |
| 6,614,039 B2 | 9/2003 | Hollander | |
| 6,656,424 B1 | 12/2003 | Deal | |
| 6,811,748 B2 | 11/2004 | Ettlinger et al. | |
| 6,813,427 B1 * | 11/2004 | Kaltenbacher | G01N 21/0303 356/300 |
| 6,921,929 B2 | 7/2005 | LeBoeuf et al. | |
| 7,027,002 B2 | 4/2006 | Takehata et al. | |
| 7,081,225 B1 | 7/2006 | Hollander | |
| 7,202,484 B1 | 4/2007 | Tantillo | |
| 7,372,044 B2 | 5/2008 | Ross | |
| 7,476,870 B2 * | 1/2009 | Hopaluk | C02F 1/325 210/748.1 |
| 7,737,457 B2 | 6/2010 | Kolodin et al. | |
| 7,838,357 B2 | 11/2010 | Bogner et al. | |
| 7,838,845 B2 * | 11/2010 | Abe | C02F 1/32 250/432 R |
| 7,875,247 B2 | 1/2011 | Clark et al. | |
| 7,989,779 B1 | 8/2011 | Ray et al. | |
| 8,029,740 B2 | 10/2011 | Hyde et al. | |
| 8,097,861 B2 | 1/2012 | Leben | |
| 8,114,346 B2 | 2/2012 | Hyde et al. | |
| 8,203,124 B2 | 6/2012 | Havens et al. | |
| 8,226,255 B2 | 7/2012 | Fan | |
| 8,347,819 B2 | 1/2013 | Lovenvirth | |
| 8,404,186 B2 | 3/2013 | Clark et al. | |
| 8,710,459 B1 * | 4/2014 | Davis, III | C02F 1/325 210/440 |
| 8,747,764 B1 * | 6/2014 | Burchman | A61L 2/0047 422/186.3 |
| 8,993,988 B2 | 3/2015 | Nathan et al. | |
| 9,293,670 B2 | 3/2016 | Toita et al. | |
| 9,548,429 B2 | 1/2017 | Shatolov et al. | |
| 9,548,431 B2 | 1/2017 | Toita et al. | |
| 9,550,004 B2 | 1/2017 | Smetona et al. | |
| 9,572,902 B2 | 2/2017 | Nathan et al. | |
| 9,687,577 B2 | 6/2017 | Dobrinsky et al. | |
| 9,696,484 B2 | 7/2017 | Dobrinsky et al. | |
| 9,703,055 B2 | 7/2017 | Dobrinsky et al. | |
| 9,855,352 B2 | 1/2018 | Dobrinsky et al. | |
| 9,987,499 B2 | 6/2018 | Hayashi et al. | |
| 10,025,028 B2 | 7/2018 | Dobrinsky et al. | |
| 10,046,075 B2 | 8/2018 | Nathan et al. | |
| 2001/0006162 A1 | 7/2001 | Hollander | |
| 2001/0025820 A1 * | 10/2001 | Morse | C02F 1/24 210/724 |
| 2003/0230977 A1 | 12/2003 | Epstein | |
| 2004/0140269 A1 * | 7/2004 | Chang | C02F 9/00 210/192 |
| 2004/0166018 A1 | 8/2004 | Clark et al. | |
| 2005/0087768 A1 * | 4/2005 | March | G01N 17/004 257/200 |
| 2005/0156119 A1 * | 7/2005 | Greene | C02F 1/325 250/436 |
| 2006/0076506 A1 * | 4/2006 | Duthie | C02F 1/325 250/436 |
| 2006/0097189 A1 | 5/2006 | Lim | |
| 2006/0120929 A1 | 6/2006 | Ward et al. | |
| 2006/0132012 A1 | 6/2006 | Sumrall et al. | |
| 2006/0138443 A1 | 6/2006 | Fan et al. | |
| 2006/0186059 A1 * | 8/2006 | Saccomanno | A61L 2/10 210/748.11 |
| 2006/0206997 A1 | 9/2006 | Chiang et al. | |
| 2007/0145292 A1 | 6/2007 | Jones | |
| 2007/0209984 A1 * | 9/2007 | Lev | C02F 1/325 210/143 |
| 2007/0256226 A1 | 11/2007 | Pinizzotto | |
| 2008/0048541 A1 | 2/2008 | Sumrall et al. | |
| 2008/0073595 A1 | 3/2008 | Thiruppathi | |
| 2008/0134420 A1 | 6/2008 | Ho | |
| 2008/0175292 A1 | 7/2008 | Sheik-Bahae | |
| 2008/0224066 A1 * | 9/2008 | Nolen | A61L 2/10 250/436 |
| 2008/0278460 A1 | 11/2008 | Arnett et al. | |
| 2009/0004046 A1 | 1/2009 | McEllen | |
| 2009/0117001 A1 | 5/2009 | Hyde et al. | |
| 2009/0191100 A1 | 7/2009 | Deal | |
| 2010/0174346 A1 | 7/2010 | Boyden et al. | |
| 2010/0242192 A1 * | 9/2010 | Backman | B01F 7/086 15/4 |
| 2010/0264073 A1 * | 10/2010 | Teng | B01F 5/0206 210/136 |
| 2010/0271802 A1 | 10/2010 | Recker et al. | |
| 2010/0320154 A1 * | 12/2010 | Ylikangas | B01D 17/0217 210/704 |
| 2010/0327766 A1 | 12/2010 | Recker et al. | |
| 2011/0022189 A1 | 1/2011 | Perry | |
| 2011/0174992 A1 | 7/2011 | Sakita | |
| 2011/0191950 A1 | 8/2011 | Liu | |
| 2011/0291995 A1 | 12/2011 | Shr et al. | |
| 2012/0011874 A1 * | 1/2012 | Conradt | C02F 1/325 62/264 |
| 2012/0144569 A1 | 6/2012 | Kodat | |
| 2012/0176241 A1 | 7/2012 | Pasch et al. | |
| 2012/0199005 A1 | 8/2012 | Koji et al. | |
| 2012/0241644 A1 * | 9/2012 | Ben-David | C02F 1/325 250/436 |
| 2014/0091230 A1 | 4/2014 | Clark et al. | |
| 2015/0060693 A1 * | 3/2015 | Lee | C02F 1/325 250/435 |
| 2015/0158741 A1 * | 6/2015 | Lee | C02F 1/325 210/184 |
| 2015/0359915 A1 * | 12/2015 | Farren | A61L 2/10 422/24 |
| 2016/0064631 A1 | 3/2016 | Shatalov et al. | |
| 2016/0114186 A1 | 4/2016 | Dobrinsky et al. | |
| 2017/0087262 A1 | 3/2017 | Toita et al. | |
| 2017/0094090 A1 | 3/2017 | Sato | |
| 2017/0095585 A1 | 4/2017 | Smetona et al. | |
| 2017/0104138 A1 | 4/2017 | Shatalov et al. | |
| 2017/0157277 A1 * | 6/2017 | Nathan | A61L 2/0047 |
| 2017/0290934 A1 | 10/2017 | Dobrinsky et al. | |
| 2017/0290937 A1 | 10/2017 | Dobrinsky et al. | |
| 2017/0340762 A1 * | 11/2017 | Ullman | A61L 2/088 |
| 2018/0104367 A1 | 4/2018 | Bettles et al. | |
| 2018/0117195 A1 | 5/2018 | Dobrinsky et al. | |

(56) References Cited

U.S. PATENT DOCUMENTS

| | | | |
|---|---|---|---|
| 2018/0117201 A1 | 5/2018 | Bettles et al. | |
| 2018/0133351 A1 | 5/2018 | Smetona et al. | |
| 2018/0135830 A1 | 5/2018 | Cai et al. | |
| 2018/0155215 A1 | 6/2018 | Torii | |
| 2018/0185529 A1 | 7/2018 | Shur et al. | |
| 2018/0221521 A1 | 8/2018 | Shur et al. | |
| 2018/0236113 A1 | 8/2018 | Gross et al. | |
| 2018/0305226 A1* | 10/2018 | Simpson | C02F 1/325 |

FOREIGN PATENT DOCUMENTS

| | | |
|---|---|---|
| JP | H0415022 A | 1/1992 |
| JP | H09-140633 A | 6/1997 |
| JP | 2005137822 A | 6/2005 |
| JP | 2005-203437 | 7/2005 |
| JP | 2006-136844 | 6/2006 |
| JP | 2006238921 A1 | 9/2006 |
| JP | 2006-263609 | 10/2006 |
| JP | 04002315 B2 | 10/2007 |
| JP | 2007/319243 A | 12/2007 |
| WO | WO-2010060079 A1 | 5/2010 |
| WO | WO-2010115183 A1 | 10/2010 |
| WO | WO-2011/083378 A1 | 7/2011 |
| WO | 20170162734 A1 | 9/2017 |
| WO | 20170162736 A1 | 9/2017 |
| WO | 2018043292 A1 | 3/2018 |

OTHER PUBLICATIONS

Japanese Office Action dated Oct. 22, 2018 in Appln. No. 2016-227384, w/English Translation, 8 pages.
European Office Action issued in EP 13855084.3 dated Dec. 16, 2020, 5 pages.
Brochure for Plexiglas G-UVT by Arkema Inc., 2 pages (2013).
Notification of Transmittal of the International Search Report and the Written Opinion of the International Searching Authority in PCT Application No. PCT/US2013/069731, dated Mar. 13, 2014 (10 pages).
HammerHead Search White & UV Flashlight, Product Model 930-011 [online]. FoxFury Lighting Solutions 2011 (retrieved on Feb. 25, 2014). Retrieved from the internet: <URL: http://www.foxfury.com/catalog/product_info.php?products_id=115>.
HammerHead Search White & UV Flashlight, Product Model 930-011 [online]. FoxFury Lighting Solutions. Wayback Machine, Jan. 5, 2012 [retrieved on Feb. 25, 2014]. Retrieved from the Internet: <URL: http:web.archive.org/web/20120105231153/http://www.foxfury.com/catalog/product_info.php?products_id=115>.
International Preliminary Report on Patentability dated May 19, 2015 in corresponding PCT Application No. PCT/US2013/069731.
Search Report issued in corresponding European Patent Application No. 13855084.3 dated Jul. 20, 2016.

* cited by examiner

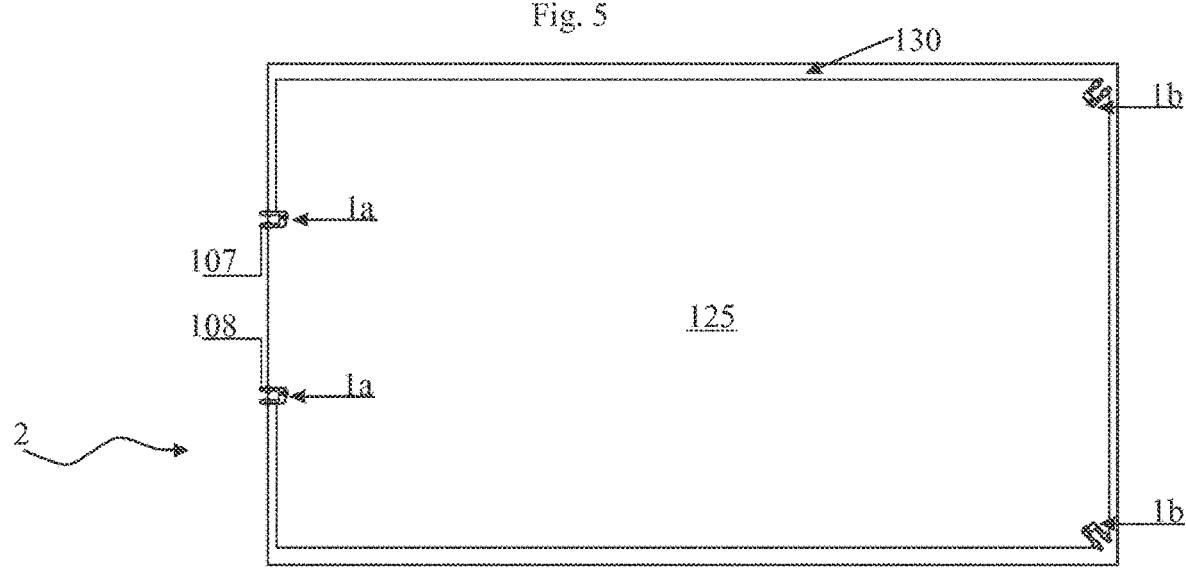

DEVICE FOR INCREASED ULTRAVIOLET EXPOSURE OF FLUIDS

CROSS-REFERENCE TO RELATED APPLICATIONS

This application is a continuation-in-part of and claims priority to and the benefit of U.S. patent application Ser. No. 15/437,199 filed on Feb. 20, 2017, which is a continuation of U.S. patent application Ser. No. 14/627,892 filed on Feb. 20, 2015, now U.S. Pat. No. 9,572,902, which is a continuation of U.S. patent application Ser. No. 14/078,288, filed on Nov. 12, 2013, now U.S. Pat. No. 8,993,988, which claims priority to U.S. Provisional Patent Application No. 61/796,521, filed on Nov. 13, 2012, all of which are hereby incorporated by reference in their entireties.

TECHNICAL FIELD

The application relates to a device and method for emitting ultraviolet (UV) light or radiation, and more particularly, to a device and method for emitting UV light or radiation over a broadcast area to sterilize and sanitize surfaces and surrounding areas and fluids.

BACKGROUND

With an ongoing need for the sanitation and disinfection of surfaces, including, but not limited to, exterior and interior surfaces inside containment vessels or other enclosed areas and/or certain fluids, UV light has been found to be an effective alternative to chemicals and germicides. Unlike many chemicals or germicides, which have been found to lose their efficacy ultimately leading to "superbugs" that are no longer responsive to said chemicals or germicides, UV light is highly effective at killing microbes, destroying their ability to reproduce, and thereby sanitizing against microbial as well as non-microbial sources (e.g., eggs, chemicals). Unfortunately, current UV devices are limited in either their efficacy, length of transmission, and/or emission spectrum. Current devices have a limited length of transmission and further require, in operation, frequent re-location as well as one or more optical filters, protective casings and/or guides for focusing and transporting the UV energy. Such devices, but dependent of low flow rates and/or requiring extended exposure times, may be acceptable for short distance transmission, such as a few millimeters, several inches or even a few feet, but cannot broadcast the full UV wavelength spectrum over a large distance with little or no gaps in exposure, especially for distances that exceeds a few feet.

There remains a need for effective sanitation and disinfection over a large area, and within liquids and/or fluids, that provides broad spectrum protection against both microbial and non-microbial sources.

SUMMARY

Embodiments disclosed herein provide functional or ornamental devices transmit UV light over a broad area and for a long distance, and extended residency times and capable of high flow rates to inactivate microbes and other pathogens as well as non-microbial sources, thereby disinfecting and sanitizing the area surrounding said devices and further minimize fouling and/or blocking of the output from the disinfecting light source. Each device may be activated by a variable or dynamic logic process that controls activation of the device, such that activation is automatic and only in the absence of one or more objects detectable by the device or alternately when a targeted object is present.

In one or more embodiments is disclosed a device for projecting ultraviolet radiation. The device includes at least one ultraviolet light emitting source emitting ultraviolet light in a wavelength range from about 10 to 400 nanometers; and a lens formed of an ultraviolet light transmissive material, wherein the at least one ultraviolet light emitting source is embedded within the lens, and wherein the lens is formed into a functional shape and does not filter the ultraviolet light emitted from the at least one ultraviolet light emitting source. The ultraviolet light transmissive material permanently embeds the at least one ultraviolet light emitting source. The ultraviolet light transmissive material may have an ornamental shape. The ultraviolet light transmissive material does not filter or refract significantly the ultraviolet light emitted from the at least one ultraviolet light emitting source. The ultraviolet light transmissive material may transmit ultraviolet light over a distance of up to 18 feet. The lens is formed in the shape of a functional element, including but not limited to a toilet seat, door hardware, handle, floor molding, and crown molding. The device may further comprise a shield. The device may further comprise or associate with a heat exchanger to dissipate heat. The device may be controlled by a variable logic process. The device may be further configured comprising a sensor to detect the presence of an object and a controller to deactivate the at least one ultraviolet light emitting source in response to the activation of the sensor. The sensor may comprise any one or more of a motion detector, infrared detector, microwave doppler detector, sound detector, vibration detector, a proximity detector, thermal detector, chemical detector, pressure detector, laser detector, magnetic detector and load cell.

Also described is a device for projecting ultraviolet radiation, such that the device is a lens and emits ultraviolet light in a range from about 10 to 400 nanometers, wherein the device is of a material that is transmissive to ultraviolet light and transmits ultraviolet light at a target. In one or more embodiments, the device is capable of focusing the ultraviolet light only on the target. The device may be activated by a variable logic process that allows activation of the device when detecting the intended object within a range selected for detection. The device is in operable communication with a detector. A further embodiment comprises a control module and a power source.

In addition, a method for providing germicidal protection by projecting ultraviolet radiation through an ultraviolet light transmissive material that forms a lens that does not filter the ultraviolet radiation, the ultraviolet radiation generated by at least one ultraviolet light emitting source embedded within the lens, the lens formed into a functional shape, the method comprising is disclosed. The method comprises providing a detector for detecting an object; in response to an absence of activity of the detector, activating a cycle of ultraviolet radiation generated by the at least one ultraviolet light emitting source; and in response to activity of the detector, inactivating the cycle of ultraviolet radiation generated by the at least one ultraviolet light emitting source. After inactivating the cycle of ultraviolet radiation and in response to an absence of activity of the detector, the method may also activate a second cycle of ultraviolet radiation. In response to activity of the detector, the method may store an identifier that is stored in a memory indicating a time of the response to activity of the detector; and iteratively apply the response to activity of the detector to a future cycle of ultraviolet radiation generated by the at least one ultraviolet light emitting source. The identifier may be applied to a next cycle to automatically affect the next cycle at a given time of day in subsequent days. The method may also validate integrity of the device to assure proper functional capability and if fault is found therein, the device will not activate Still further, described is a method for projecting ultraviolet radiation from a device through an ultraviolet light transmissive material forming a lens of the device such that the lens does not filter the ultraviolet radiation, the ultraviolet radiation generated by at least one ultraviolet light emitting source that is disposed within the ultraviolet light transmissive material to project ultraviolet light beyond the device to a selected object, the method comprising providing the device with a control module operating a logic-based algorithm from a processor, operably linking the control module to a detector, running the control module for a period of time to determine activity of the detector, allowing the logic-based algorithm to obtain data associated with activity of the detector, and transmitting ultraviolet light based on the activity of the detector. The device is operable by a power source. The device detector may be sensitive to the object. The ultraviolet radiation is projected toward the object.

In additional embodiments is described a method of providing germicidal protection by projecting ultraviolet radiation through a device comprising an ultraviolet light transmissive material that forms a lens that does not filter or refract significantly the ultraviolet radiation, the ultraviolet radiation generated by at least one ultraviolet light emitting source embedded within the lens, the lens formed into a functional shape, the method comprising: providing the device with a control module operating a logic-based algorithm from a processor; operably linking the control module to a detector; running the control module for a period of time to determine activity of the detector; allowing the logic-based algorithm to obtain data associated with activity of the detector and absence of activity of the detector; and transmitting ultraviolet light based on the data associated with the absence of activity of the detector.

According to some embodiments, a device for disinfection of fluids is provided by projecting photonic radiation throughout a device, the device having an ultraviolet light transmissive material that forms a lens that does not filter or refract significantly the photonic radiation, the photonic radiation generated by at least one light emitting source embedded within the lens, the lens formed into a functional shape. The device has an embedded photonic source within the surrounding lens such that the composition of the lens is flexible and remains transmissive to sanitizing radiation by resisting degradation from ultraviolet and external contaminates, including solvents, and resists external buildup of elements which may block light transmission. Further, the device enables extended residency time of greater than 10 seconds for fluids within a containment vessel and further induce a vortex upon the internal fluids, so as to produce effective disinfection of the fluids passing through the device even at high flow-through rates. In some embodiments, the ultraviolet light transmissive material is composed of fluoropolymers.

According to other embodiments, a method of disinfecting fluids is provided by projecting photonic radiation through a device having an ultraviolet light transmissive material that forms a lens that does not filter or significantly refract the photonic radiation. According to some embodiments, the photonic radiation is generated by at least one light emitting source embedded within the lens, the lens optionally formed into a functional shape. In other embodiments, the method includes embedding the photonic source within the surrounding lens such that the composition of the lens remains functional and does not readily foul and/or become externally covered in contaminates which require removal, including either by manual and/or mechanical cleaning processes or replacement of components to restore the unit to unimpeded light output. According to embodiments disclosed herein, the device permits extended residency time of fluids within a containment vessel, so as to produce effective disinfection of the fluids passing through the device even at high flow rates.

BRIEF DESCRIPTION OF THE DRAWINGS

Various embodiments will be explained in more detail with reference to the drawings in which:

FIG. 5 depicts a front view of another representative device described herein;

FIGS. 6A-6F illustrate representative UV light emitting sources or packages suitable for operation with a device described herein;

FIG. 14b is a perspective view of the light bar of FIG. 14a

DETAILED DESCRIPTION

Figure 1:
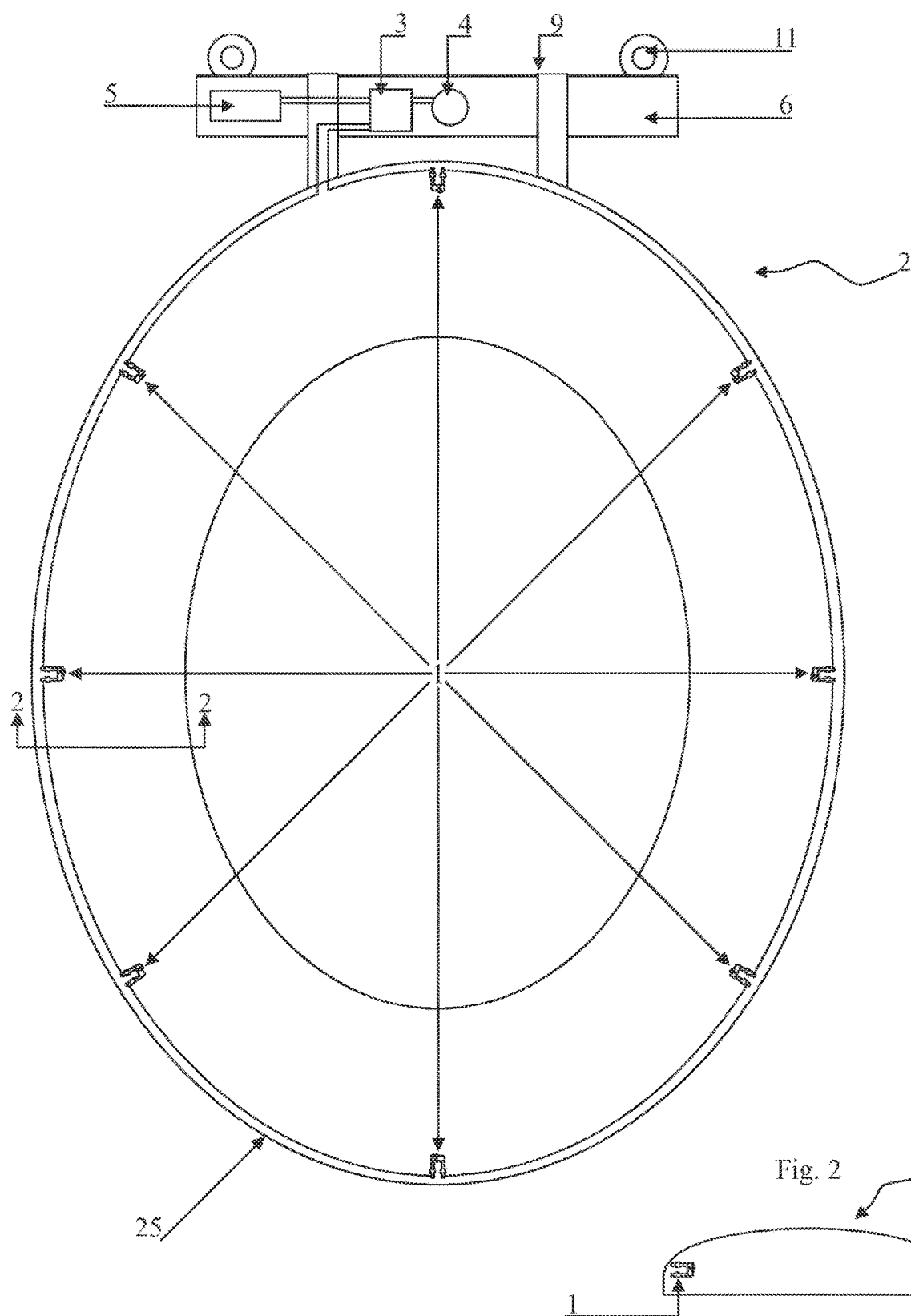
FIG. 1 depicts a top view of representative device described herein.
Figure 2:
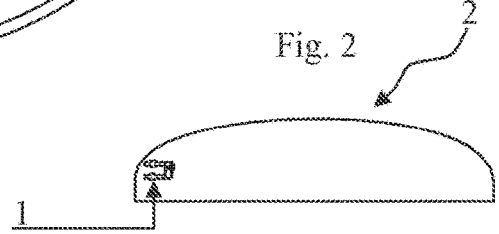
FIG. 2 depicts a cross-sectional view of FIG. 1 at line 2-2.

Although making and using various embodiments are discussed in detail below, it should be appreciated that as described herein are provided many inventive concepts that may be embodied in a wide variety of contexts. Embodiments discussed herein are merely representative and do not limit the scope of the invention.

In the embodiment depicted in FIGS. 1-4, a representative device 2 is illustrated in the form of a toilet seat 25. In the embodiment illustrated in FIGS. 1-4, device 2 includes a plurality of ultraviolet (UV) light emitting sources or packages 1 disposed or otherwise embedded within the toilet seat 25 to project UV radiation or light therethrough and outwardly therefrom in order to sanitize, disinfect and/or decontaminate the surface of the device 2 and its surrounding areas. As illustrated and as otherwise described herein, the device 2 is formed of a UV light transmissive material, which not only supports the UV light emitting sources 1, but also focuses photons emitted by the UV light emitting sources 1. While the device 2 is formed in the shape of a toilet seat 25, it should be understood that the UV light transmissive material may be formed into any number of desired functional or ornamental shapes, such as, for example, door hardware (handles, push plates, push bars, knobs, etc.), faucets, sinks, picture frames, crown molding, telephones, light fixtures, shower enclosures, bathtubs, dishwasher liners, washer and dryer tubs, handrails, handles, cases and enclosures, furnishings, toys, electronic devices, or any other type of device or object. The methods of forming the functional or ornamental shape of the device 2, and in particular, the shape of the UV light transmissive material, are well known in the art, and may include injection molding, heat processing, vacuum or cold forming, laser or water processing, extrusion, 3-D printing, and the like. The exact material selection considers factors such as the necessary strength, durability and flexibility, as well as heat properties required of the device when placed in the desired location for use.

By embedding the UV light emitting source 1 in the UV light transmissive material, there is little to no degradation of the light. Thus, there is no blockage or unintentional redirection of the UV light and very little change in incident angle, thereby allowing the device to project light at significantly longer distances. The UV light transmissive material is preferably one that minimizes refraction and photonic deflection, enabling the projection of photons over a large area and for very long distances. As a result, the device 2 is an improved UV light emitter with a longer broadcast range for the UV light as compared with typical UV light emitters. The UV light transmissive material used herein, when ornamentally shaped, provides an ornamental purpose to the device 2 while also offering sanitizing, and disinfecting action as well as biocidal activity against pathogens and microbes over a large broadcast area. Similarly, the UV light transmissive material, when functionally shaped, provides a functional purpose to the device 2 while also offering sanitizing, and disinfecting action as well as biocidal activity against pathogens and microbes over a large broadcast area. With selection of the UV light transmissive material, in many embodiments, there will be little or negligible degradation of the UV light transmissive material with use.

In the embodiments disclosed herein, any UV light transmissive material may be used that is permeable to UV light rays. Examples include, but are not limited to, clear plastics, such as those that are chemically simple, containing generally carbon, fluorine, and/or hydrogen atoms (e.g., fluoropolymers). In addition, other clear plastics from the group of acrylates and polyacrylates (e.g., polymethylmethacrylate), cyclic olefin copolymers, polyimide quartz, polyetherimides, amorphous polyolefins, polycarbonates, polysytrenes, polyethylenes, are suitable, or when modified to provide an acceptable permittivity to UV light. The materials may be further selected for resistance to heat and will generally exclude additives that block UV transmission. Furthermore, the materials may be readily selected for strength and durability or other mechanical features when used for functional purposes. Other exemplary UV light transmissive material include, but are not limited to, silicates (fused silica, crystallized quartz), sapphire, and magnesium fluoride. Because transparency of many plastic materials may be dependent on their thickness, in some embodiments, a thinner material may be preferred to improve transmission of the UV light. In addition, when a thicker material is desired, the one or plurality of UV light emitting sources 1 disposed or embedded in the UV light transmissive material may be so disposed or embedded as to have little or only a thin layer of the light transmissive material near the top surface of the UV light emitting sources 1.

According to some embodiments, an ultraviolet light transmissive lens material can include a fluoropolymer. The unique performance characteristics of fluoropolymers, which make fluoropolymers advantageous in various applications, include an increased resistance to high operating temperatures, including for example, up to approximately 450 degrees Fahrenheit, and increased resistance to damage from many chemicals and solvents, including alcohol, ethanol, petroleum compounds, acetone, acids, alkaline bases, and others. As a result of the highly stable composition of fluoropolymers, fully submerged systems can be utilized, which resist and/or otherwise substantially reduce fouling or build-up of contaminants on the outside of the disinfecting light source that can block the transmission of disinfecting light. This is a common problem in typical UV light water disinfection units. It requires the light source, which is typically inside a containment vessel, to be cleaned. In many cases this limits the ability of the units to be effective, since heat build-up and/or mineralization/build-up of contaminants thereon oftentimes causes premature failure of the unit. Further, fluoropolymers readily transmit, ultraviolet energy, including for example, wavelengths down to approximately 190 nm. Fluoropolymers also resist degradation to ultraviolet radiation, which readily destroys and damages other common polymers. Fluoropolymers are oftentimes approved for use in medical and food applications and are commonly considered non-flammable, as they self-extinguish if exposed to open flames. Unlike other disclosed materials, fluoropolymers are flexible and can be readily formed into numerous shapes. Fluoropolymers can be heat-sealed onto light sources to both protect the light source from external damage and tampering, but remains flexible, which presents a superior characteristic when compared to fragile materials, such as, for example, common glass. Further, this material can be formed into helical coils, which when submerged in fluids or disposed within a vessel or container, can both induce a consistent flow rate and also create a vortex imparted upon the fluid. The vortex provides greater consistency in relative position of fluids within the space (i.e., a more predictable/optimized flow pattern to the fluid within the vessel in relation to both time and distance to the operable source as well as it relates to flow). It is this consistency which can be utilized to increase residency time within the space to create longer exposure times to disinfecting light that can increase efficacy, while also maintaining high flow through rates. Typical current systems can have residency times as short as slightly over 1 second for an 80 gallon per minute unit. This rapid flow rate, which depending on turbidity, fluid contamination, dissolved minerals, and other factors present in fluids can prevent adequate exposure time to disinfecting light to produce the desired level of germ load reduction within the targeted fluid including, but not limited to, water, solutions, and contaminated fluids. By utilizing a device in which the photonic source is embedded within the surrounding lens such that the lens is flexible and remains transmissive to sanitizing radiation by resisting degradation from ultraviolet and external contaminates including solvents, and resists external buildup of elements which may block light transmission, increased efficiencies. Further, and as discussed in further detail below, the device can permit an extended residency time of greater than 10 seconds for fluids within a containment vessel and further induce a vortex upon the internal fluids passing through the inside of the coiled lens. This produces effective disinfection of the fluids passing through the device even at high flow through rates, and represents a better, more effective system for the consistent disinfection of fluids.

Permanently disposing or embedding in the UV light transmissive material also protects the UV light emitting source 1 from environmental factors, damage, and tampering. Permanently embedding at least one UV light emitting source 1 in the UV light transmissive embedding material allows the device 2 to retain and transmit close to or nearly 100% of its energy and hence improves light output. The UV light transmissive material, in a sense, has been transformed into a single operative lens for the UV light emitting source 1, and will, therefore, distribute the UV light not only for a much longer distance because of the minimal difference in refractive index (when transmitting through only a UV light transmissive material), the single lens can distribute photonic energy throughout the entire lens, thereby the UV light propagation, in the absence of any purposefully positioned shield or reflector or absorber, will be 360 degrees, hence omnidirectional, from a single UV light emitting source 1. This represents a significant improvement over existing devices.

Figure 3:
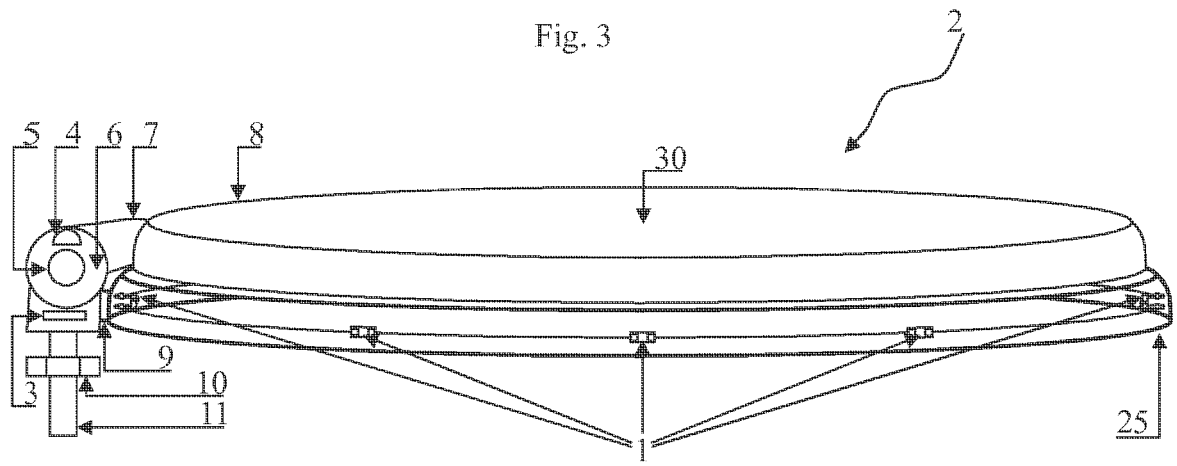
FIG. 3 depicts a side view of the device of FIG. 1 which further comprises a cover or shield.
Figure 4:
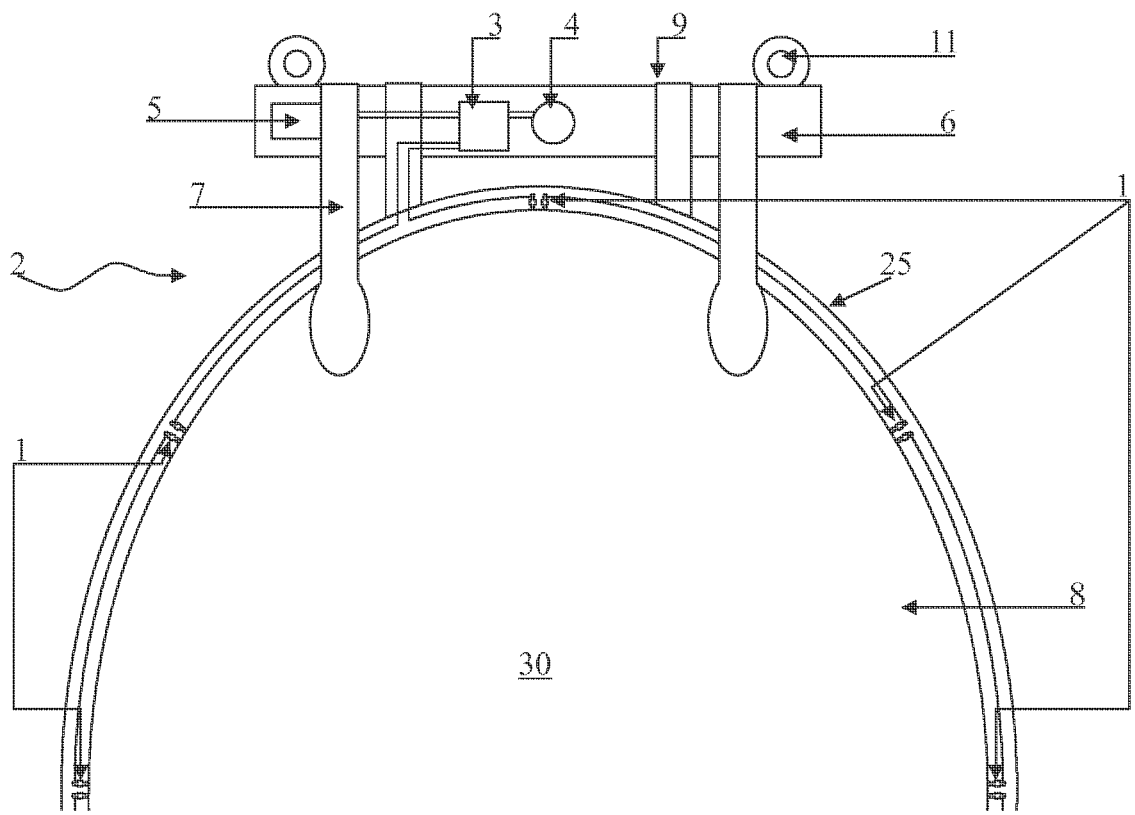
FIG. 4 depicts a partial top view of the device of FIG. 3.

In one or more embodiments, such as that depicted in FIGS. 1, 3 and 4, the broadcast area by device 2 is uniform over the entire shaped peripheral surface of toilet seat 25 and the light emits and project omnidirectionally from the surface of the device. This pattern is extremely beneficial and provides a significant improvement over existing devices that degrade the UV light before it leaves the surface of such devices and that often provide only a narrow, limited spectrum of UV light. The efficacy of the UV light transmitted from a device described herein is a great improvement when compared with other existing devices because there is a greater cumulative amount of UV light that is transmitted to any object within a large and operative radius around the device, which is required to effectively kill pathogens and microbes on said object(s). The greater cumulative amount of UV light also means that the duration of UV light exposure may be reduced as compared with the duration required with a comparative device having a lower UV light output. In addition, the omnidirectional capability of the device 2 means that movement or relocation of the device is not required in order to adequately sanitize, disinfect, or decontaminate said object(s) and their surrounding area.

As illustrated specifically in FIGS. 1-4, the UV light emitting sources 1 are positioned near a side surface of the device 2 (i.e., embedded in seat 25). In operation and as discussed above, the seat 25 acts as a single lens for the plurality of UV light emitting sources 1. According to some embodiments, the toilet seat 25 further includes a cover or shield 30, which may be threadably mounted to a toilet (not illustrated) with fasteners 11 and locking nut 10 (or any other suitable means for fastening) to enable quick attachment (see, e.g., FIG. 3). In the embodiments illustrated in FIGS. 1, 3 and 4, the toilet seat 25 includes eight light emitting sources 1 that are circumferentially spaced around the toilet seat 25; however, it should be understood that a greater or fewer number of UV light emitting sources 1 may be incorporated into the toilet seat 25. For example, in some embodiments, only a single UV light emitting source 1 may be utilized. In other embodiments, a greater number of UV light emitting sources 1 may be utilized and positioned at any location within the toilet seat 25. In further embodiments, one or a plurality of UV light emitting sources 1 may be positioned on the cover or shield 30. Placement of UV light emitting sources 1 may often depend on where the device 2 will be positioned in its environment. For example, if a device 2 is mounted to a wall, then UV light emitting sources 1 may only be necessary on front facing surfaces of the device 2. Referring specifically to FIG. 3, the cover 30, when included, is configured to attach via a hinge 7 for raising and lowering cover 30. When UV light emitting sources 1 are activated, cover 30 will be exposed to UV light and as a result, will be sanitized and disinfected. When the cover 30 comprises a UV light absorbing (or blocking or reflecting) material, it will absorb (or block or reflect) UV light transmission, preventing further transmission through the cover 30. In other embodiments, the cover 30 may be in whole or in part made of a UV light transmissive material. Thus, cover 30 may be designed, as desired, to absorb, block or otherwise influence the direction and extent of UV light transmission from the device 2. The device 2 may, in some embodiments be powered by power source 5 or may be mobile, operating from a battery or other portable power source.

FIG. 5 illustrates another representative device 2 comprising a plurality of UV light emitting sources 1a and 1b. Like device 2 of FIGS. 1-4, device 2 of FIG. 5 acts as a single lens for the plurality of UV light emitting sources 1a and 1b. UV light emitting sources 1b are fully embedded in the UV light transmissive material. UV light emitting sources 1a are embedded in part, as will be described in more detail below. Both UV light emitting sources 1a and 1b are embedded in a front plate 125, which is made of a UV light transmissive material. The front plate 125 is supported by back plate or shield 130. In one embodiment of FIG. 5, back plate 130 is not a UV light transmissive material. For example, the back plate 130 may be made of a reflective material, thereby enhancing propagation of photons in a front-ward and side-ward direction only, such that photons propagating towards back plate 130 are reflected back towards front plate 125 and outwardly away from the front and side faces of the front plate 125. In this example, the device 2 is suitable for use as a hardware component on a door, wall, or furniture. The device 2 is optimally positioned when there is little or no requirement for sanitizing, disinfecting, or otherwise decontaminating objects that are located behind back plate 130. The device 2 of FIG. 5, may also, in some embodiments be powered by a power source (not shown) or may be mobile, operating from a battery or other portable power source.

While not shown, a device described herein may further have other uses. For example, a device described herein may be a medical device or be coupled to a medical device. Similar to the device 2 depicted in FIGS. 1-5, any such medical or other device will have a UV light emitting source permanently embedded in whole or in part in a UV light transmissive material, in such a manner that the UV light transmissive material acts as a single lens to direct the UV light. In some embodiments, such as when the device is for medical purposes, the device may be designed to focus the UV light towards a specific object and/or location. Because some devices may necessitate a higher output of UV light, suitable portions of such devices may also include a shield and may optionally include a heat exchanger, such as a passive heat sink known in the art. In some embodiments, the shield will redirect at least some of the UV light to focus the UV light when emitted from the device. In some embodiments, the shield will block at least some of the UV light to prevent damage when in certain regions near the device. In some embodiments, the shield will potentiate at least some of the UV light to improve output of the UV light when emitted from the device. Any of said shields may be used alone or in combination and may be made integral with the device or be near the device.

Figure 8:
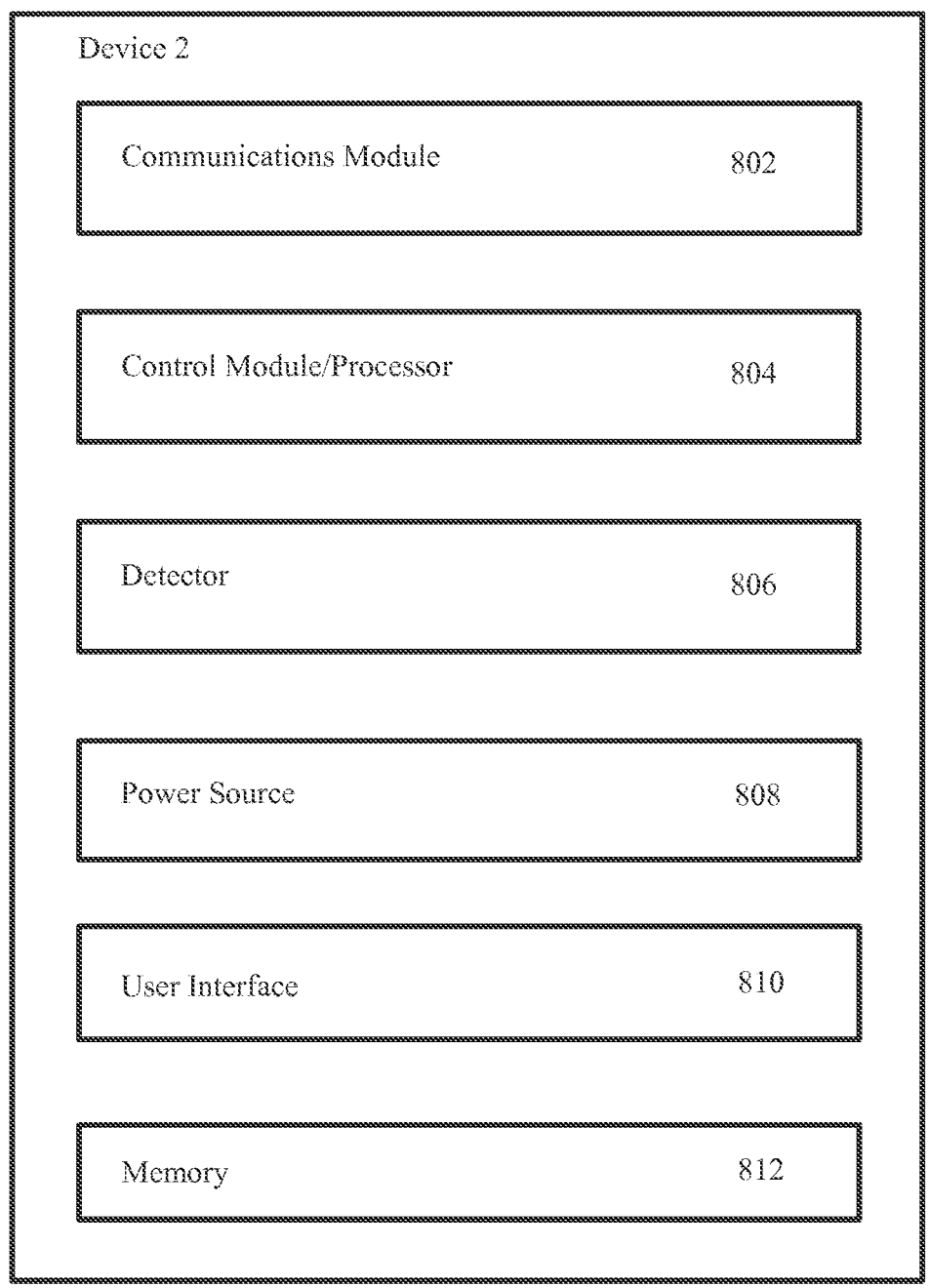
FIG. 8 depicts a representative block diagram of a device described herein.

Referring again to FIGS. 1, 3 and 4, the UV light emitting sources 1 are powered by power source 5, such as, for example, an AC, DC, solar, induction, wind and/or battery power source or fuel cell. UV light emitting sources 1a and 1b of FIG. 5 are similarly powered. Power source 5 may, in some embodiments, be a variable power source, which may be used, for example, to vary the light output of device 2. The UV light emitting sources 1, 1a and 1b, are further operably linked (wired or wirelessly) to a control module 3. Control module 3 is operably associated (wired or wirelessly) with at least one detector 4. The control module includes at least one data storage unit or memory that may or may not be portable. The data storage unit stores programmed instructions, data or both. The control module 3 optionally includes a wireless communication interface (e.g., via transceiver chip or the like) that may be integrated or provided as an additional component. A processor, generally associated with control module 3, controls many operations of the device. Said operations include storage of data, instructions for and communications with the one or more UV light emitting sources 1 (as well as UV light emitting sources 1a and 1b), as well as instructions for and communications with a user interface. The processor may also retrieve and execute instructions stored in the at least one data storage unit, such as memory (e.g., one or more of random access memory, flash memory, and the like). Thus, the control module 3 receives input from the at least one detector 4 and from the user interface, sends output to the one or more UV light emitting sources 1 (including 1a and 1b) and may send output via the user interface. User input may be in the form of buttons or from a keypad or an LCD screen and combinations thereof. In some embodiments, the control module may provide output to the user, such as in the form of a display or one or more status indicators. FIG. 8 depicts the various modules that may be associated with a device 2 as described herein, including communications module 802, control module/processor 804, detector 806, power source 808, user interface 810, and memory 812. It is understood that some of said modules, such as the control/processor 804, detector 806, power source 808, user interface 810 and memory 812 may be included on the device 2 itself and/or remote from the device 2.

As illustrated in the embodiments of FIGS. 1, 3 and 4, the controller 3, the detector 4, and the power source 5 are located in a hub 6, which is disposed on or adjacent to device 2; however, it should be understood that other locations are acceptable, such as on the seat 25, the cover 30 or any other location. The locations may be within device 2, near device 2, adjacent to the device 2 or may be some distance away, such as when configured with components that allow for remote or wireless operation. According to some embodiments, the controller 3 may include an LCD screen or other suitable means for controlling and/or setting conditions of operation, for displaying output and allowing user input.

Detector 4 may include one or more of a motion detector, an infrared sensor, a sound detector, a device for detecting vibration, a proximity detector, a thermal detector, a chemical detector, a doppler microwave detector, a pressure detector, a load cell, a laser detector, magnetic or any other device or method of detection of an object or person so as to avoid and prevent, as explained in greater detail below, unwanted exposure to UV light.

In operation, the device 2 communicates with the at least one detector 4, which is operably associated with device 2. In one or more embodiments, when the detector 4 fails to detect an object to which it is responsive to, such as a person or other moving object in its effective area, the UV light emitting sources 1 may be activated (or will continue to remain active). For example, when detector 4 is a motion sensor and senses motion typically associated with a human proximate to the device 2, the detector 4 communicates with the control module 3 and a signal or other output is generated by the control module 3 to deactivate and otherwise turn off the UV light emitting sources 1 in order to avoid and/or otherwise minimize exposure to the UV light. The detector 4 may be calibrated as to how sensitive it is in detecting the object to which it is responsive to (e.g., object or person). In some embodiments, a plurality of detectors 4 may be required, such as when a device 2 is very large (e.g., long or wide) or when the device 2 is required to operate in a large space. The plurality of detectors 4 may be the same type of detector or different types. Thus, detector 4 acts as an interlocking unit operatively coupled for inactivation of UV light emitting sources 1 when the detector 4 is activated. This provides an improved process for operating the UV light emitting sources 1, allowing them to function safely, optimally and in an operative manner for their intended purpose, to sanitize, disinfect and decontaminate the effective area on and around device 2.

Said detector 4 may also be any of said detection devices or methods of detection of an object or person so as to provide a predetermined and specific emission of UV light. In these embodiments, when detector 4 detects an object to which it is responsive to, such as an object in the range of sensitivity of the detector 4, the one or more UV light emitting sources 1 may be activated. Said one or more UV light emitting sources 1 may continue to remain active until the object is no longer in the range of sensitivity of detector 4. Alternatively, said one or more UV light emitting sources 1 may be inactivated after a predetermined period of time.

In addition to detecting the presence of the object or person, the detector may be communicatively coupled to another object, such as a door, building power, or any other device or system that is capable of enabling the system to detect or determine the presence or likely presence of the object or person near or proximate to the device 2. For example, in the event device 2 is a toilet seat 25, detector 4 may be communicatively coupled to the restroom entranceway to detect a door moving from a closed position to an open position in order to inactive device 2 prior to the object or person entering the restroom. Upon activation of detector 4, a signal is generated to deactivate the UV light emitting sources 1. Similarly, detector 4 could be selected and used to detect whether or not a restroom light is on or off and a resultant signal generated by the control module 3 to activate the UV light emitting sources 1 only when the light is off, presumably when the bathroom is not occupied.

As explained in greater detail below, activation and deactivation of light emitting sources 1 (as well as that of UV light emitting sources 1a and 1b) are controlled by a dynamic (variable) logic process and algorithmic instructions associated with controller 3, and may be stored in the at least one data storage unit.

Any of devices 2 of FIGS. 1-5 or any other functional or ornamental device described herein, will have one or a plurality of UV light emitting sources 1. As illustrated in FIGS. 6A-6E, the UV light emitting source 1 may resemble and include some but not all components of a typical light emitting diode (LED), or modifications thereof, thereby resembling, for example, a TO-39 (see FIG. 6B, FIG. 6C), a surface mounted diode (see FIG. 6D), a TO-38 (not shown) or a P8D type (not shown), etc. The UV light emitting sources 1 of FIGS. 6A to 6D are generally configured with a semiconductor device or package with at least one semiconductor chip or die 103. When the UV light emitting source 1 is designed to resemble any of the typical LEDs, the chip or die 103 will comprise a p-n junction. The UV light emitting sources 1 may also, in some embodiments, resemble and include components of a typical laser emitting diode (see FIG. 6E).

Similar to a typical or traditional LED die or laser diode, any of the UV light emitting sources 1 of FIGS. 6A to 6F will include a UV light emitting material as part of the UV functional portion. However, unlike typical LED dies that have a UV light emitting material on the die that is either white or monochromatic and in the visible spectrum (generally from 450 nm to 940 nm), the UV light emitting material described herein, such as that on die 103 of UV light emitting source 1 in FIGS. 6A to 6D or associated with UV light emitting source 1 of FIG. 6E to 6F, will emit in the ultraviolet light spectrum, from between about 10 nm to 400 nm (ionizing and non-ionizing UV), including emission in the germicidal range of between about 265 nm to about 280 nm. The UV light emitting material described herein may be a solid material or a gas. FIG. 6A to 6E comprise solid UV light emitting materials. In these embodiments, the solid UV light emitting material is a component of the die 103 or laser diode 114. Examples of UV light emitting materials include nanocrystals, of variable shape and size, or combination of nanocrystals that emit within the ultraviolet light spectrum or only within a portion of the ultraviolet light spectrum. Further examples include tin dioxide nanocrystals covered with a shell of tin monoxide; aluminum nitride with or without pseudomorphic epitaxial structures or layers; gallium nitride with or without pseudomorphic epitaxial structures or layers; cerium doped with lithium strontium aluminum fluoride; boron diamonds; etc. The light emitting material may, therefore, be one or a plurality thereof (or any suitable combination of light emitting materials) that emit over a broad spectrum, or one or a plurality (or any suitable combination of light emitting materials) that emit over a narrow spectrum (e.g., monochromatic). FIG. 6F comprises a gaseous UV light emitting material, as is known to one skilled in the art.

The amount of the light emitting material may be varied in order to vary the intensity or light output. The light output may also be varied by the amount of power to the UV light emitting source 1 of FIGS. 6A to 6F, supplied by the power source, and hence, to the UV light emitting material.

In various embodiments, one or more semiconductor chips or dies 103 comprising the UV light emitting material are mounted in a cavity 102. The cavity and/or its associated configuration may be such that the direction of propagation of UV light ranges from about 20 degrees to as much as 150 degrees. In FIG. 6A, cavity 102 is located atop the anvil 106 and is wire bonded with wire 101 that resides on the post 105 spaced apart from the anvil 106 with a gap 104 there between. The anode 107 is connected to the post 105 and the cathode 108 is connected to the anvil 106, and jointly the anode 107 and cathode 108 together are referred to as the leadframe. Power is supplied to the UV light emitting source 1 by a power supply, similar to the power supply 5 of FIGS. 1, 3, and 4. This configuration of components is similar to components used for a typical or traditional LED. In FIG. 6B, the semiconductor chip(s) 103 comprising the UV light emitting material are depicted above cathode 108 with anode 107 to the right; however, additional variable leadframes may also be included with this configuration and may serve as mounting points. In FIG. 6D, one or more semiconductor chip(s) 103 comprising the UV light emitting material are centrally located, while the anode 107 and the cathode 108 are positioned peripherally. In FIG. 6E, a UV light emitting source 1, a laser diode comprising a UV light emitting material is shown comprising a photodiode pin 109, a photodiode wire 110, a photodiode 111, a laser diode pin 112, a laser diode 114 and a laser diode wire 113. In FIG. 6F, a UV light emitting material, in the form of a gas emits from fluorescent bulb 115, in which an anode 107 and cathode 108 are only partially embedded in the UV light transmissive material.

Similar to the embodiments of FIGS. 1-5, each the UV light emitting materials (either associate with a chip or die, a laser diode, or a bulb, as depicted in FIGS. 6A to 6F, will be wholly embedded in the UV light transmissive material, in order that the UV light transmissive material forms a lens. While the UV light emitting materials are wholly embedded within the UV light transmissive material, additional components of the UV light source 1 are not always embedded, as was previously described with UV light sources 1a of FIG. 5.

In all embodiments described, UV light emitting materials, by way of their UV light emitting further are controlled by a control module in operable communication with a detector. Associated with any of the UV light emitting sources 1 of FIGS. 6A to 6F may be one or a plurality integrated circuits or discrete components, when more than one UV light emitting source 1 is controlled at a time. In some embodiments, when the UV light emitting source 1 includes two or more chips or dies 103, they may be connected together in an inverse parallel configuration. This allows light spectral variability, including colors when one or more chips emit in the visible light spectrum or include one or more phosphor or color coating agent. In some embodiments, when a plurality of dies 103 are included, they may be controlled independently. For example, one UV light emitting source may include at least one die with a UV light emitting material and one die with a material that emits in the visible light spectrum. In operation, the dies 103 may be controlled independently in order that the UV light emitting material is inactive when the material that emits in the visible light spectrum is active, and vice versa. In another example, a device may have at least one UV light emitting source as well as a visible source that emits in the visible light spectrum. Here, the at least one UV light emitting source is controlled independently in order that the UV light emitting material may be inactive when the visible source (that emits in the visible light spectrum) is active, and vice versa.

None of the UV light emitting sources 1 (including 1a and 1b of FIG. 5 or as otherwise described herein) require added photonic crystals or an added reflection device, or an added metal grating structure for coupling or for operation. In some embodiments, the UV light emitting source 1 is also not encapsulated in or beneath a spaced apart lens or shell. Thus, in these embodiments, there is no air between the UV light emitting source 1 and the UV light transmissive material to induce a change in refractive index as the energy is emitted from the UV light emitting source 1. Furthermore, in these embodiments there is no additional lens, including one of a different refractive index or of a different or non-UV light transmissive material, that prevents passage of photons at certain angles or that change light output or minimize projection of UV light. This is contrasted with the typical or traditional LED that has a cap or lens and, therefore, has air in its immediate proximity, which exhibits a low refractive index, immediately adjacent the LED components. The cap or lens in a typical or traditional LED often uses epoxy as the lens material. However, epoxy is not permissive to most of the UV light spectrum; it is generally only transmissive to wavelengths greater than 350 nm, thereby blocking transmission of lower wavelengths, including the germicidal wavelengths (~265 nm to about 280 nm) known as UV-C. UV light passing through an epoxy lens will also degrade the epoxy irreparably over a relatively short period of time. In addition, most epoxy caps or lenses are cap or cone shaped. An epoxy cap or lens (or one of another material having a higher refractive index or different refractive index than the UV light transmissive material) will diffuse the UV light, forcing it to emit at only certain angles, generally at higher incident angles at only portions of the lens, because of the shape of the cap or lens.

In additional embodiments, the UV light emitting source 1 may include a native lens. In these embodiments, the native lens is preferably made of a UV light transmissive material as described herein. The native lens is fused or otherwise bonded with the UV light transmissive material of the device, which, therefore, forms the single functional lens of the device. Thus, there is little, minimal or no change in refractive index when emitting UV light through the single functional lens (UV light transmissive material), such that UV light emission still benefits fully by having the single lens. With such a configuration remains no need for photonic crystals or an added reflection device, or an added metal grating structure for operation.

While light output is a function of and varies with the type of chip, it is also dependent on the transmissibility of the UV light transmissive material. A more focused light output with a larger or narrower spatial radiation pattern may be created by adjusting the current supplied to the LED and altering the shape, shielding or transmissibility of the UV light transmissive material. This means the light output and the light distribution may be controlled and finely tuned by changing the material properties and/or thickness of the UV light transmissive embedding material. For example, the UV light transmissive material containing the at least one UV light emitting source 1 may be sandwiched between a second material that is less transmissive to UV light or one that blocks UV light transmission. Various arrangements of UV light transmissive material and non-UV light transmissive material or less UV light transmissive material may be provided to a device described herein. The surface characteristics of the UV light transmissive material may also be manipulated to vary the surface characteristics, such as the incident angle of light, which assists in light output. For example, in some embodiments, all or part of the surface of the UV light transmissive material may be shaped with facets, or angles, to allow more light to be emitted from the surface and to minimize any internal reflections that may be caused when the surface is flat. The ultraviolet light transmissive material may also have an abraded surface to maximize light transmission.

In any of the devices described herein, embedding of the UV light emitting source includes embedding the UV functional portion (the UV emitting material) in the UV light transmissive material as well as embedding, either partially or fully, leadframes 107, 108 in the UV light transmissive material and optionally embedding, either partially or fully, any shield. As depicted in FIGS. 1-4, the UV light emitting sources 1 are fully embedded in the UV light transmissive material of seat 25. In FIG. 5, UV light emitting sources 1b are fully embedded in the UV light transmissive material of front plate 125, the UV light emitting sources 1a are only partially embedded. With partial embedding, the entirety of die 103, cavity 102, wire 101, post 105 and anvil 106, and gap 104 are embedded in the UV light transmissive material of front plate 125. Leadframes 107, 108 are only partially embedded, exposing the anode and cathode respectively. In additional embodiments, embedding as described herein may also include the control module 3 with or without the detector 4.

The depth of embedding in the UV light transmissive material may vary. Variables that may impact the depth of embedding include the function, location and type of force that may be applied to the UV light emitting source 1 and the UV light transmissive material when formed as a functional or ornamental device. A UV light emitting source 1 may in some embodiments be positioned at a depth that is in a range of about ⅛ inch to 2 inches or more below the outer surface of the UV light transmissive material. For example, a UV light emitting source 1 in a push plate may be about ⅛ inch below the outer surface of the UV light transmissive material. A UV light emitting source 1 in a toilet seat may be about ½ inch below the outer surface of the UV light transmissive material. A UV light emitting source 1 in a door handle may be about ¾ inch below the outer surface of the UV light transmissive material.

In any of said embodiments, whether fully or partially embedding the UV light emitting source 1, there will be minimal, negligible or no spatial separation between the UV light emitting source 1 (UV emitter) and the UV light transmissive material (lens). Hence, there will be no gap or significant difference in transmissibility or refractive index because of an added, non-transmissive material. Instead, the UV light emitting source 1 (UV emitter) and the UV light transmissive material (lens) are directly coupled or associated without the need of an intermediate or additional component required in alternative emitters, such as photonic crystals, an added reflection device, or an added metal grating structure. With the devices described herein the UV light emitting source 1 (UV emitter) and the UV light transmissive material (lens) are a singular inseparable functional device 2 when in operation with the control module 3, the detector(s) 4, the power source(s) 5 and optional shield(s).

The logic circuitry associated with the control module that will generally include one or more of the following: microprocessor, printed circuit board, logic circuit, microcomputer, CPU, and interfaces that may be remote (based on radio frequency, Wi-Fi, infrared, laser, and/or internet). The logic circuit includes a problem solving (temporal learning) logic, as depicted visually in FIG. 7, which activates the UV light emitting source 1 embedded in the UV light transmissive material (lens) of the described device. The problem solving logic is, thus, an algorithmic and iterative logic activation process to initiate activation as well as inactivation of the device.

Figure 7:
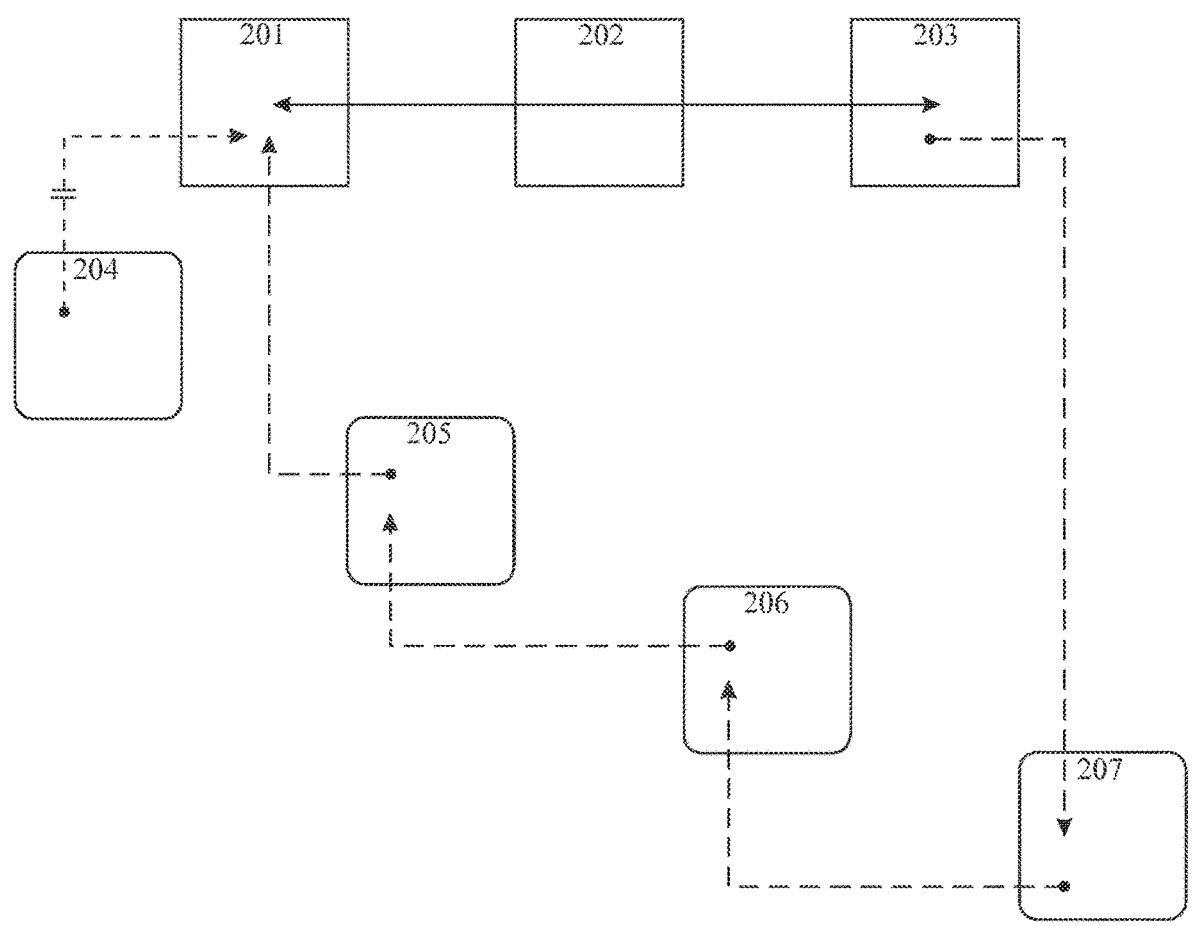
FIG. 7 depicts a logic process as described herein.

As depicted in FIG. 7, the rule set for an activation cycle includes On 201, Off 202, and the Variable 203. The solid line between 201, 202 and 203 represents event states while dashed lines flowing from 203 and 201 and between 207, 206, and 205 represent data. In an example of the iterations performed by the described device, an activation cycle will initiate with data from the Initial Program 204 directing the activation potential of On 201, Off 202, and the Variable 203. The Initial Program 204 directs control module 3 on device 2. As previously stated, the control module 3 may be onboard the device 2 or remotely controlled. Upon direction from control module 3 by the Initial Program 204, the device 2 will activate one or more UV light emitting sources 1. However, when detector 4 is activated, because there is motion, sound or other activity created by a presence within the detection range of detector 4, this activates the Variable 203 event, thereby activating the Off 202 state. Cumulative data from both the successful directions of control module 3 (e.g., successful activations of the one or more UV light emitting source(s) 1 by the Initial Program 204 and the unsuccessful directions of control module 3 (interrupted activations of the one or more UV light emitting source(s) 1 by Variable 203 event, and triggering the Off 202 state), may be captured as data. In some embodiments, the data is stored data 207. Some of the stored data may be processed by a dynamic program 206. Processing may include an algorithm that determines an optimal frequency and duration of successful activations of the one or more UV light emitting source(s) 1 in a certain period of time (e.g., 24 hour period). This ensures that the one or more UV light emitting source(s) 1 are not active when detector 4 is activated, which is representative of an object or a presence within an effective sensitivity of detector 4, and hence device 2. This also provides a method of allowing the device 2 to automatically activate for a full exposure cycle without requiring manual input and without projecting harmful UV light on the object or the presence. When the dynamic program 206 is finished processing the data, a new program is communicated to the active program 205, which now directs the On 201, Off 202, and Variable 203. The Initial Program 204 is then set to a state of stasis. This process is generally iterative. It may, in some embodiments, continue indefinitely, or may be set to continue for only a set number of iterations. In additional embodiments, the logic may only include the On 201, Off, 202 and Variable 204 state only or any combination of logic previously described above.

With the algorithmic logic activation process, the one or more UV light emitting source(s) 1 will be activated in the absence of an object or presence, which means only as long as the detector 4 remains inactive. Moreover, with the described process, UV light emitting source 1 will be inactivated (if active) when detector 4 is activated, such when there is an object or a presence in the range or sensitivity of detection of detector 4. The process may further accommodate additional programs and algorithms. The algorithmic logic activation process may also be stacked. The algorithmic logic activation process may include additional logic that varies the activation length of the UV light emitting source 1, such that there may be certain activations that are of a long duration and certain activations that are short in duration. For example, a short duration may be activated more often while a long duration may occur less frequently. The durations may also trigger only a subset of UV light emitting source 1. For example, UV light emitting source 1 may be triggered for only a short duration to kill pathogens and microbes that are destroyed after only short durations of exposure to UV light. UV light emitting source 1 may also be triggered for a long duration to kill molds, fungi and algae that are destroyed only with long durations of exposure to UV light. Any variabilities may be written into the dynamic program 206, calculated as a potential logic response to high traffic times as well as times of long absences of Variable 203 events. Similar logic may also be applied to alter the UV light intensity.

Figure 9:
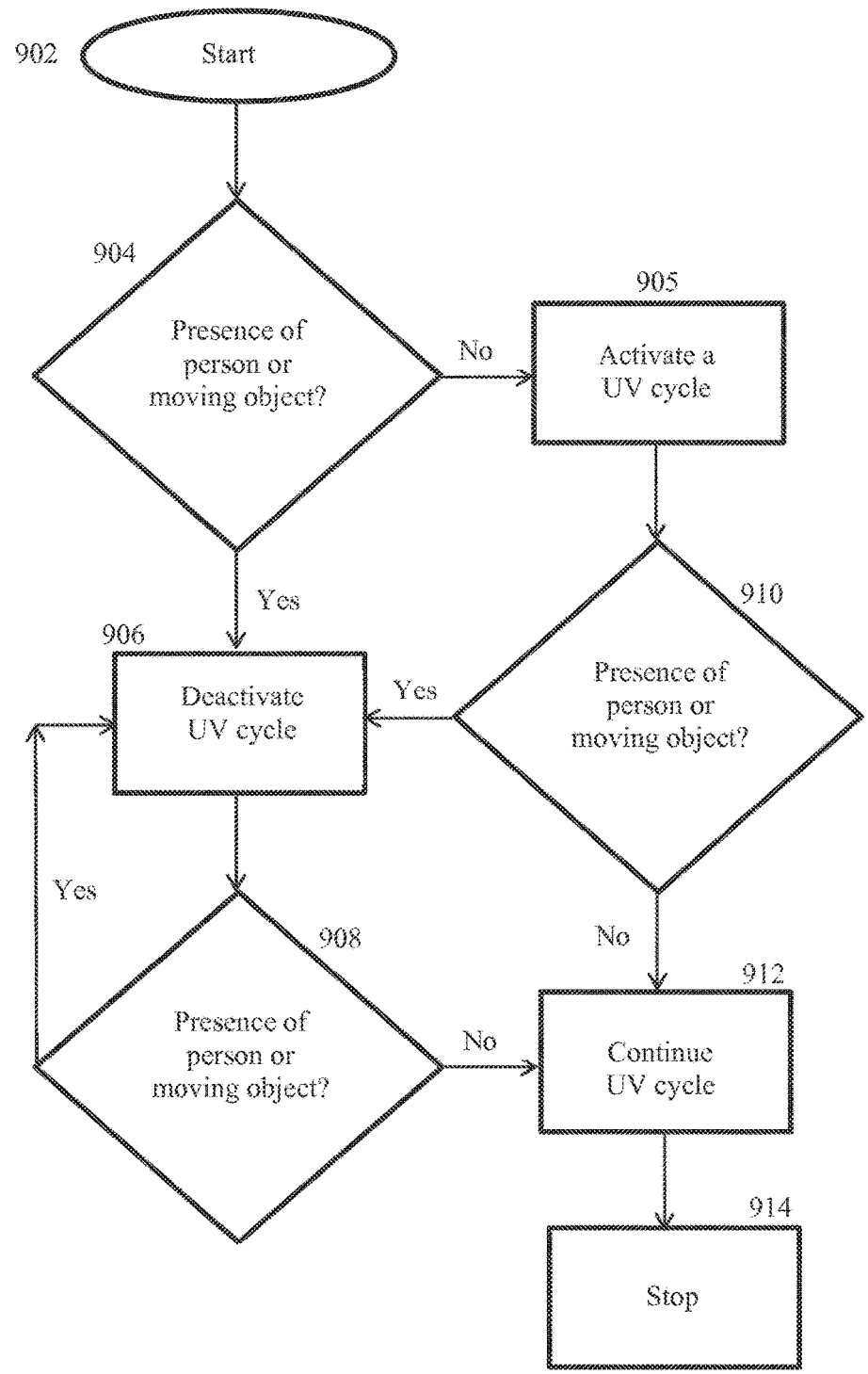
FIG. 9 representative flow chart of another representative logic process described herein.
Figure 10:
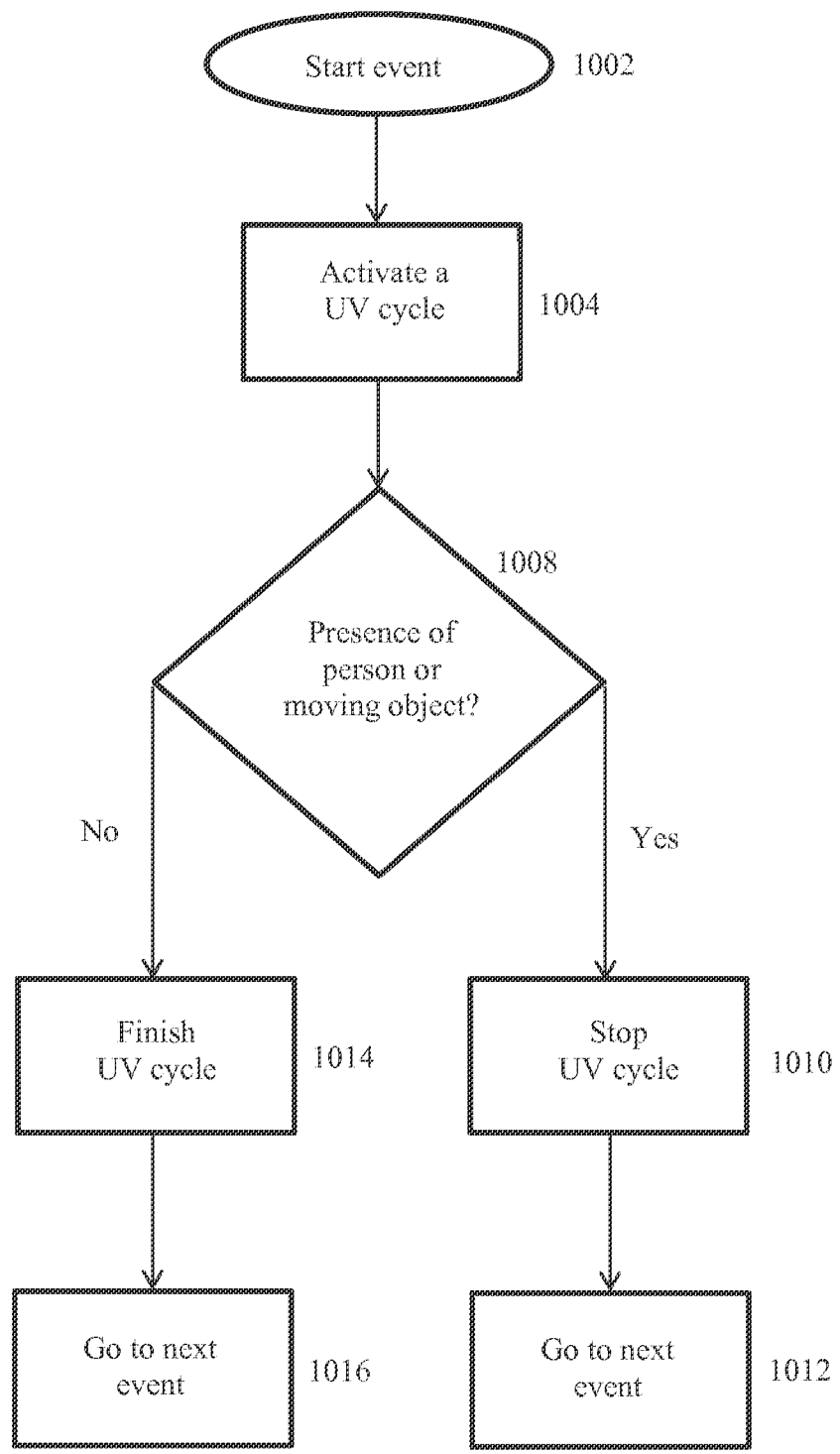
FIG. 10 depicts a representative flow chart of still another representative logic process described herein.

FIGS. 9 and 10 provide examples for activation of devices described herein. While the examples reference a detector as a motion detector, this is merely exemplary of any type of detector suitable with the process. And the examples do not limit the number or types of detectors that may operate as described. Referring first to FIG. 9, a logic process of a device is initiated at 902 and the device emits radiation from a UV light emitting source 1 for a predetermined UV cycle at 905 (predefined duration, intensity, and time of day) only when there is no detection at 904 by detector 4 of a person or moving object. When there is no detection at 910 by detector 4 of a person or moving object, the UV cycle will continue and finish its cycle at 912 and stop at 914. When there is detection at 904 of a person or object, by detector 4, a UV cycle is deactivated at 906. Similarly, if during the active cycle 905 there is detection of a person or object by detector 4, there is also deactivation of the UV cycle at 906. The detector may continue to be prompted until there is no further presence of a person or object at 908 and the cycle is continued at 912 and stopped when complete at 914.

Referring to FIG. 10, in some embodiments, a process starts at 1002 and the device emits radiation from a UV light emitting source 1 for a predefined UV cycle at 1004. The cycle continues and is complete at 1014 if there is no presence of an object or person at 1008. The cycle is stopped prematurely at 1010 if the there is a presence of an object or person at 1008. Whether or not the cycle is completed at 1014 or stopped prematurely at 1010, the process will automatically move to the next predefined event at 1016 or 1012, respectively.

Figure 13A:
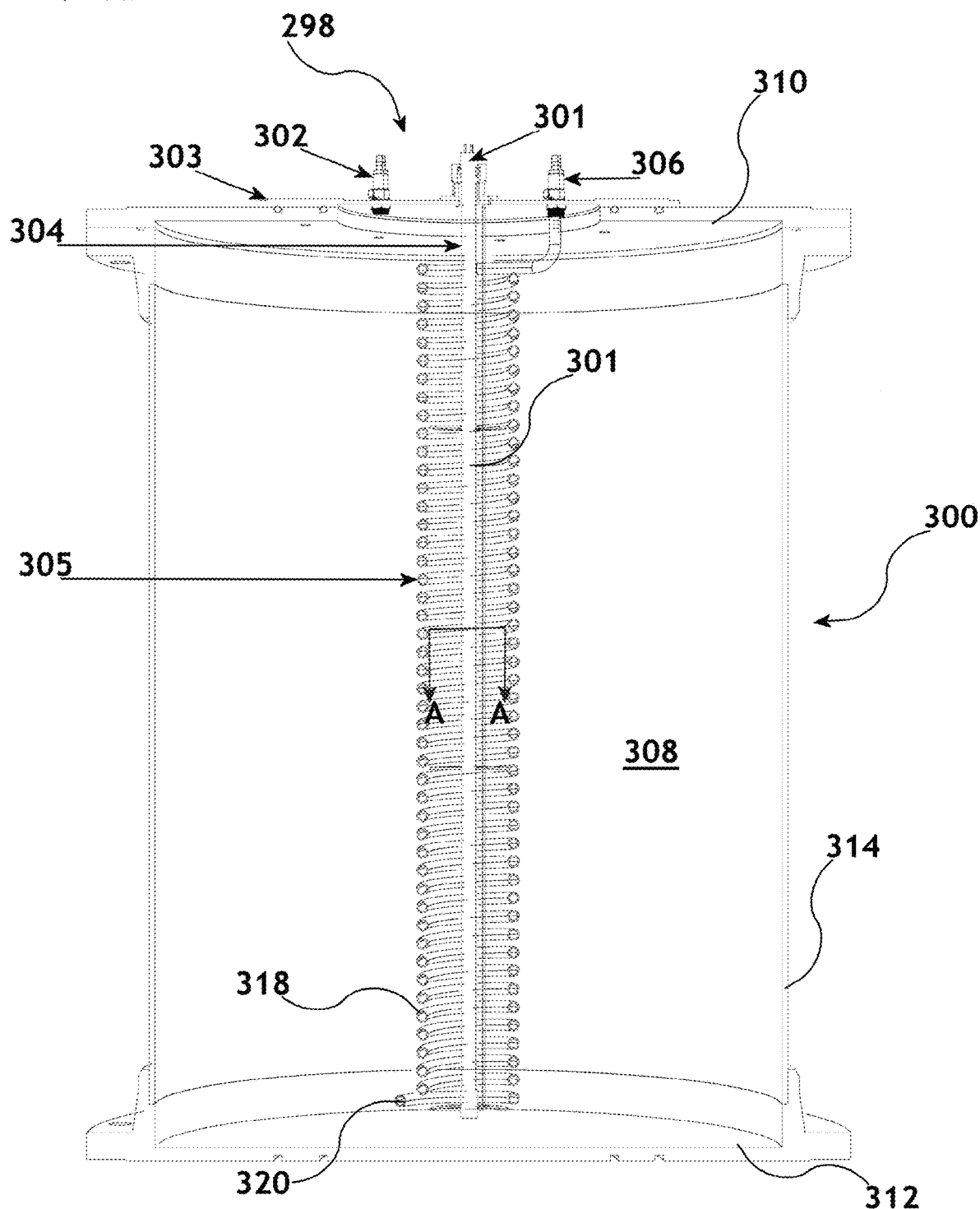
FIGS. 13a and 13b are illustrations of a containment vessel for disinfecting fluids passing therethrough.
Figure 13B:
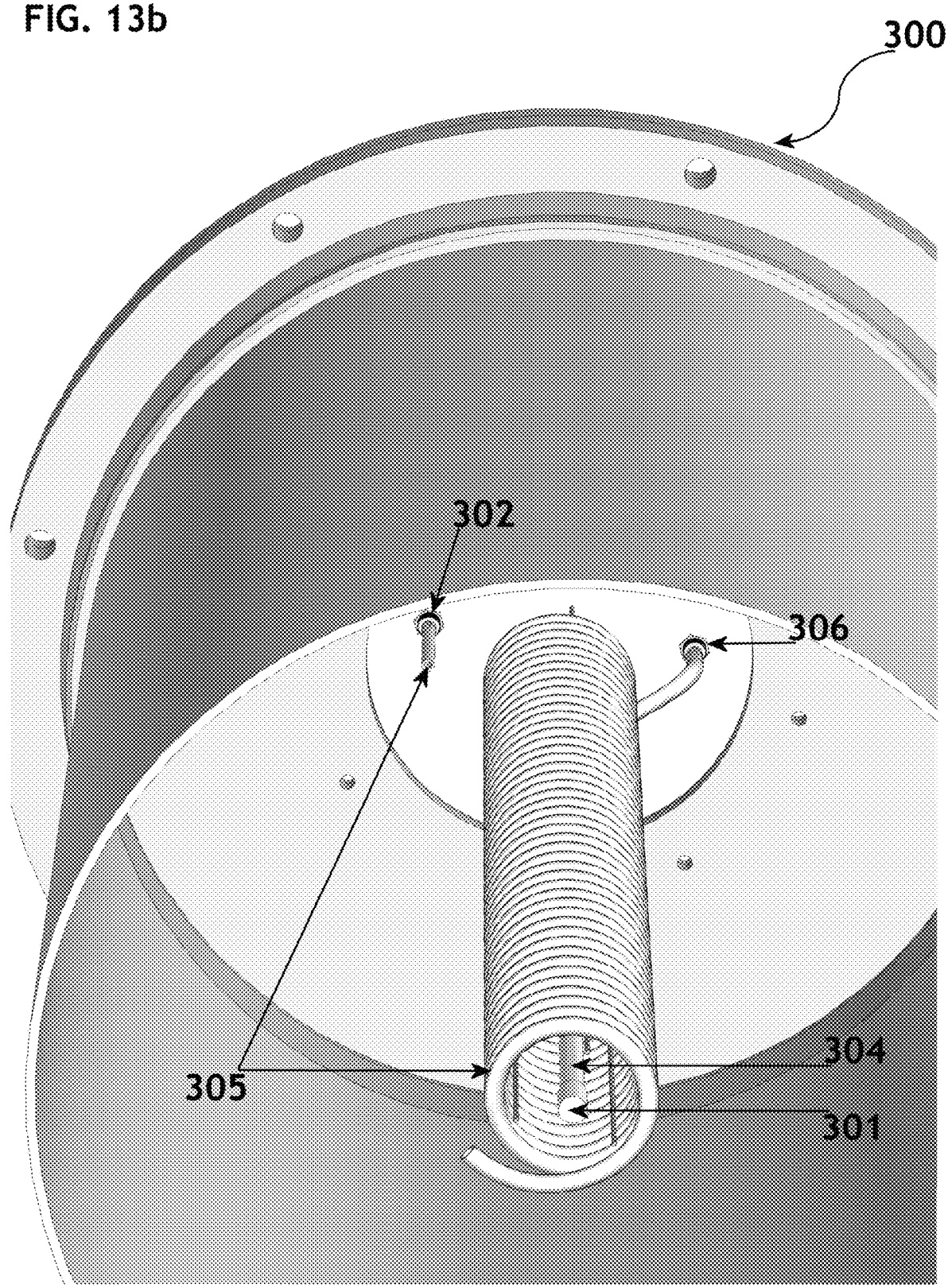

Referring now to FIGS. 13a and 13b, a sterilization system 298 is illustrated in which a light source 301 is disposed within a containment vessel 300 to sanitize fluids flowing therethrough. In FIGS. 13a and 13b, the sterilization system 298 includes the containment vessel 300, the light source 301 and a fluid conduit 305 disposed therein. As discussed in greater detail below, fluid is directed from a fluid inlet 306 directly into the conduit 305. The fluid exits the opposed end of the conduit 305 and into the vessel interior 308, where the fluid is sanitized prior to exiting the vessel through the outlet 302, which may in some embodiments require passage through an additional length of conduit 305 as shown, for example, in FIG. 13b. In operation, the light source 301 is powered so as to generate photonic energy to, as discussed below, sterilize the fluid as it flows through the conduit 305 and into the vessel interior 308 for eventual exit through outlet 302.

In the embodiment illustrated in FIGS. 13a and 13b, the containment vessel 300 is cylindrical having a top wall 310 an opposed bottom wall 312 and a sidewall 314 extending between the top wall 310 and the bottom wall 312. The top wall 310 includes a removable cover 303 to provide access to the vessel interior 308. According to one embodiment, the containment vessel 300 is approximately 50 inches tall and has a diameter of approximately 27 inches so as to have a volume to receive approximately 100 gallons of fluid in the interior 308. It should be understood, however, that other sizes and shapes of the containment vessel 300 may be utilized. For example, non-circular cross sections, such as, for example, square, rectangular, octagonal and/or oval, may be utilized. In addition, the containment vessel 300 may be built with differing heights such as for example, a height less than or greater than 50 inches and having diameters less than or greater than 27 inches. As explained in greater detail below, the size and the shape of the containment vessel 300 is selected based at least in part on certain variables such as the time necessary to expose the fluid to the photonic energy, desired flow rates, desired amount of turbidity (or lack thereof), and desired fluid flow paths within the vessels interior 308. The desired shape and flow rate may be defined by the targeted sanitizing effect and end-use application, including fluid storage, fluid treatment, fluid purification, chemical mitigation, contaminated fluids, etc. including those which require ultraviolet to inactivate, detoxify or otherwise change the chemical nature of various contaminates including chemical and petroleum contaminates. The desired shape and flow rate may also be dependent upon the location of the system, including, but not limited to, restaurants, hospitals, laboratories, food and beverage production facilities, manufacturing locations such has those that utilize CNC machines, offices, buildings, residences, hotels, cruise ships, municipalities, military, law enforcement, governmental agencies including disaster and emergency service, etc.

Figure 13C:
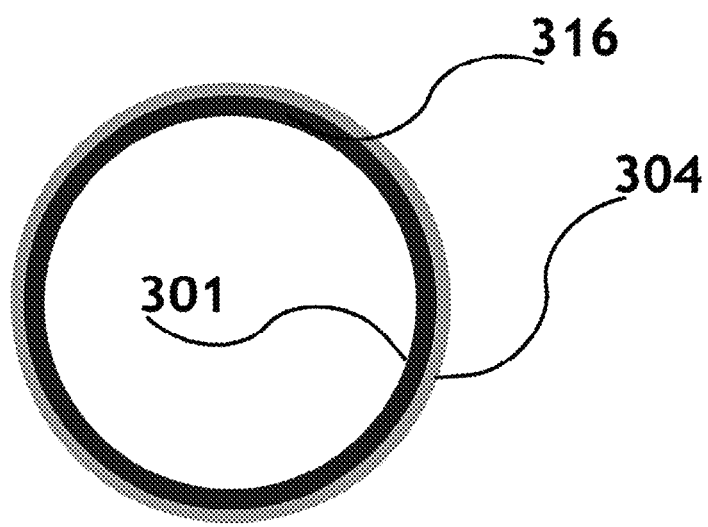
FIG. 13c is a cross sectional view of a light source illustrated in FIG. 13a taken along the line A-A.

Referring specifically to FIG. 13c, the light source 301 is coupled to and in direct and immediate contact with an ultraviolet transmissive lens 304 in order to permit the generated photons, inclusive of any generated ultraviolet light, to freely propagate throughout the entirety of the lens 304 and into the vessel interior 308. For example, in the embodiment illustrated in FIG. 13c, the lens 304 encircles an outermost surface 316 of the light source 301. According to some embodiments, the light source 301 is a 75-watt UV-C 254 nm type bulb. The surrounding lens 304 has a thickness of 0.02 inches, although other types of light sources 301 and lens thicknesses can be utilized. According to some embodiments, the lens 304 is formed of a ultraviolet light transmissive material such as, for example, a fluoropolymer.

In the embodiment illustrated in FIGS. 13a and 13b, the fluid conduit 305 is a coiled tube, which is shown submerged within the surrounding fluid to be sanitized in the vessel interior 308 and is disposed around the submerged light source 301. As illustrated in FIG. 13a, the conduit 305 has a circular cross-sectional area forming a fluid passageway 318, although other shapes can be utilized for the fluid passageway 318. In some embodiments, the fluid passageway 318 has a diameter of 0.74 inches and a wall thickness of 0.06 inches and is formed having a total uncoiled length of 40 feet. According to some embodiments, the fluid conduct 305 is coiled with 46 turns and has a coil outer diameter of approximately 4 inches. It should be understood that the fluid conduit 305 may be of different sizes, shapes, thicknesses and having a different number of turns depending on factors such as size of the vessel 300, amount of photonic energy generated, desired exposure time, flow rates through the vessel 300, etc.

In operation, the light source 301 and surrounding lens 304 are submerged within the fluid inside the vessel interior 308 and the conduit 305 is positioned such that the light source 301 is disposed inside the coils. The surrounding lens 304 encloses and protects the light source 301 from elements in the fluid that may damage the submerged components or otherwise adversely impact the performance of the sterilization system 298. Such damaging elements may include harsh chemicals, dissolved compounds and other debris that may be present in the fluid being sanitized (i.e., metal, particulate, plant matter, etc.). In addition, the lens 304 resists any significant damage and/or degradation caused by ultraviolet light and/or heat generated by the light source 301. Due to the highly stable composition of fluoropolymers, it is possible to create fully submerged systems, such as the system illustrated in FIGS. 13a and 13b, which resist fouling or a build-up of contaminants on the outside of the disinfecting light source that may ultimately block the transmission of disinfecting light.

In use, fluid is directed into the conduit 305 through the vessel inlet 306. In the embodiment illustrated in FIGS. 13a and 13b, fluid flows through the coiled conduit 305, and thus, around the light source 301, ultimately exiting into the vessel interior 308 the conduit exit 320, which is disposed adjacent to or otherwise near the bottom wall 312, at a constant flow rate. Advantageously, the constant flow rate provides a non-turbulent and constant flow while at the same time creating a vortex imported on the fluid. This flow produces consistency in both flow rate, as well as greater consistency in relative position of fluids within the vessel 300. It is this consistency that can be utilized to increase residency time within the space to create longer exposure times to disinfecting light. This can increase efficacy while maintaining high flow through rates. Typical systems can have residency times as short as slightly over 1 second for an 80 gallon per minute unit. This rapid flow rate, which depending on turbidity, fluid contamination, dissolved minerals and other factors present in fluids, can prevent adequate exposure time to disinfecting light to produce the desired level of germ load reduction within a targeted fluid, including water, solutions, and even contaminated fluids, to name a few.

It should be understood that by embedding the photonic source 301 within the flexible surrounding lens 304 of fluoropolymeric material, the system 298 remains transmissive to sanitizing radiation by resisting degradation from ultraviolet and external contaminates, including solvents, and resists external buildup of elements which tend to block light transmission.

Embodiments disclosed herein permit an extended residency time of greater than 10 seconds for fluids within a containment vessel and further induce a vortex upon the fluids passing through and exiting the inside of the coiled tube so as to produce effective disinfection. Fluids passing through the device even at high flow through rates, represents a better, more effective system for the consistent disinfection of fluids. According to embodiments disclosed herein, this may be achieved by modulating the flow of incoming liquids into the vessel 300 through the inlet 306. Additionally, the diameter of the inlet 306, the size of the helical coils 305 (diameter of fluid passageway, diameter of coils, number of coils, as well as the size of the outlet 302 can independently or in combination be altered to increase or decrease flow through rates throughout the containment vessel 300.

According to some embodiments, both the ultraviolet transmissive lens 304 as well as the conduit 305 may be manufactured utilizing ultraviolet transmissive lens materials, which when fully submerged within the vessel 300, provides multiple exposure intervals to liquids passing through the conduit 305 as well as upon the exit into the vessel interior 308 from the sanitizing photons generated by the light source 301. For example, fluid is exposed to sanitizing photons generated by the light source 301 not only when inside the conduit 305, but also when fluid exits the conduit 305 and travels through the vessel interior 308 and to the exit 302. The generated ultraviolet light/photons project in an omnidirectional pattern throughout the entirety of the fluid passing through the conduit 305 and vessel interior 308. This multiple exposure characteristic permits for longer duration exposure times to more effectively sanitize the targeted liquids by increasing both exposure time, but also proximity to the light source which can be varied to increase efficacy of the device. It should be understood that more than one light source 301 and/or conduits 305 may be utilized in a sterilization system, depending on flow rates, volume of the sterilization system and other factors.

Figure 14A:
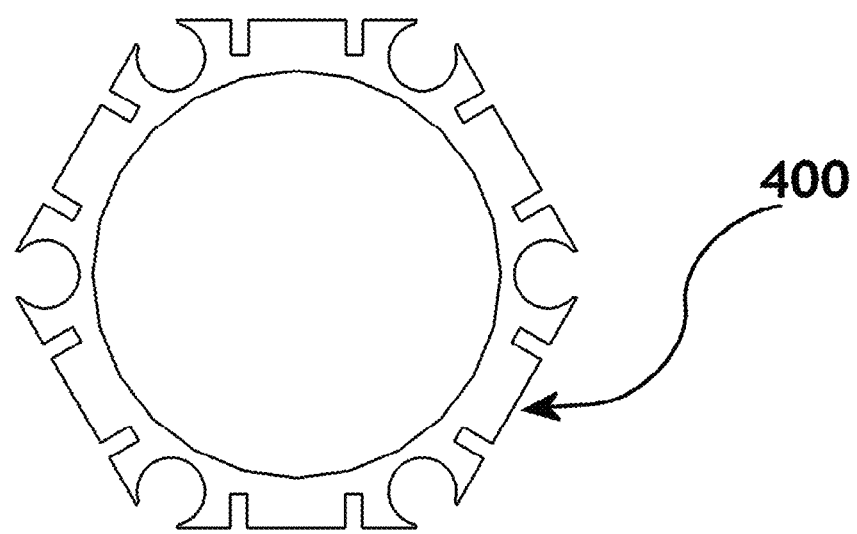
FIG. 14a is a side view of a light bar.
Figure 14B:
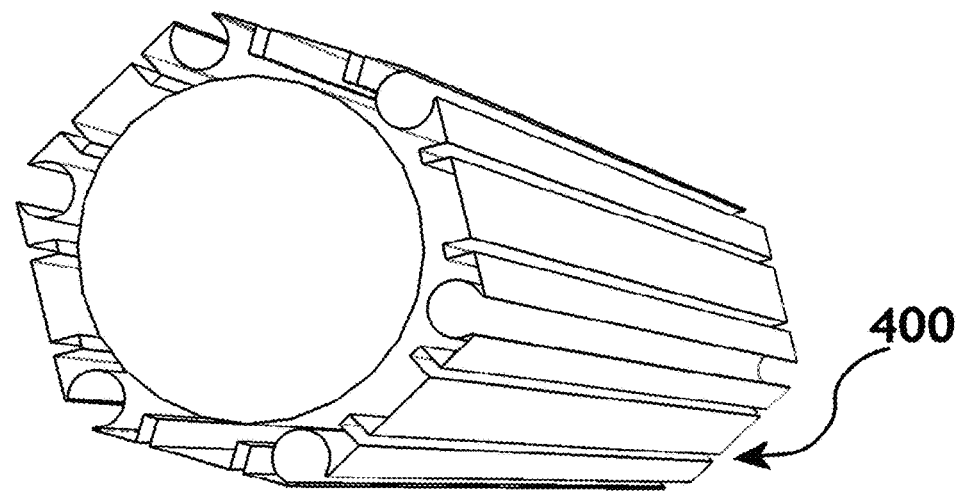
Figure 14C:
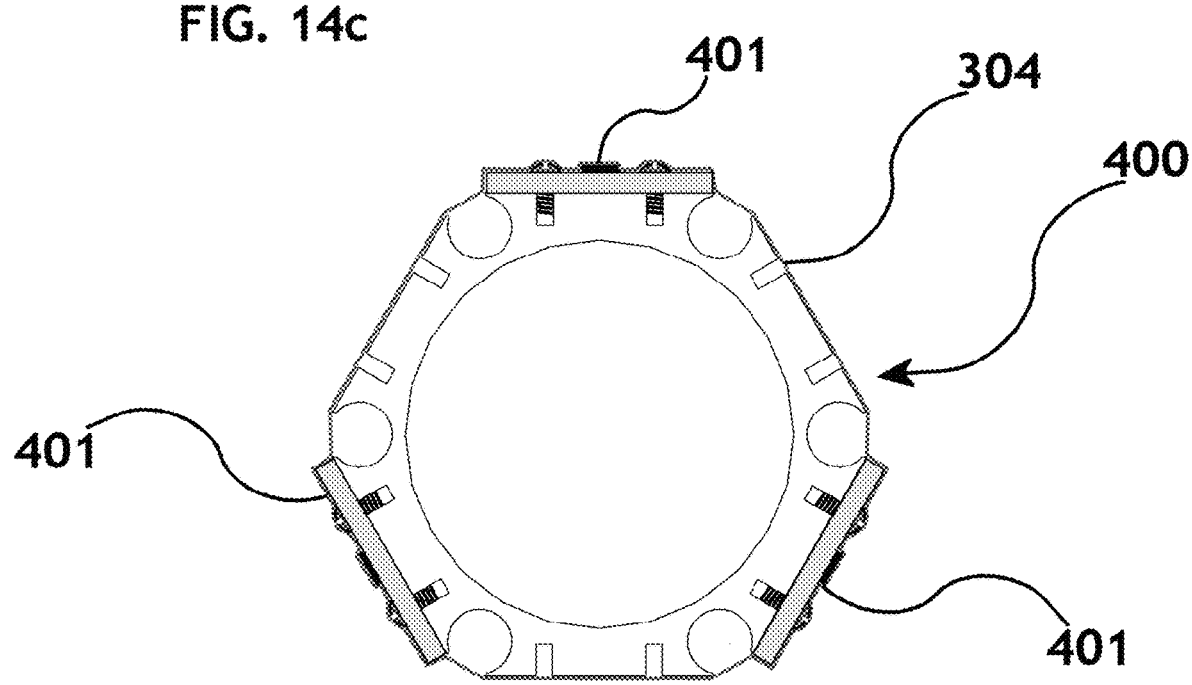
FIG. 14c is a section view of the light bar of FIGS. 14a and 14b with a light source mounted thereon.

FIGS. 14a-14c illustrate a light bar 400 for supporting a light source 401 thereon. In the embodiment illustrated in FIGS. 14a-14c, the light bar 400 serves multiple functions. For example, the light bar 400 can be fabricated from a material so as to, in addition to supporting the light source 401, act as a heat sink for the light source 401, as well as act as a rigid mounting surface for the application and/or coupling of the ultraviolet transmissive lens 304 thereto, as best illustrated in FIG. 14c. In the embodiment illustrated in FIGS. 14a-14c, the light bar 400 includes six sides for supporting one or more light sources 401 thereon. It should be understood that the light bar 400 can have a greater or fewer number of sides, depending on the desired configuration. The light bar 400 is unique in that it permits for the variance of populating one or more sides with one or more light sources so as to selectively generate and direct sanitizing photonic energy as required. The light bar 400 may be configured to have light sources 401 mounted upon one, two, three, four, five or six sides, in an alternating, continuous or intermittent pattern. Further, each light source 401 can be varied, both individually or relative to each side to generate differing frequencies of photonic energy to achieve the desired level of sanitization of the targeted liquid.

The described devices 2 are suitable for use in any environment, such a home, office, business, hospital or the like. Activation of the device 2 or any embodiments thereof, will sanitize and disinfect the environment in which they are in and for a distance of up to 18 feet or more. Because of the broad spectrum nature of the device 2, it is germicidal and is operative whether a material in the environmental is airborne, liquid, solid or frozen.

Thus, as described herein, device 2 may be considered a singular entity that is both a UV emitter and a UV lens for transmitting UV light, in a wavelength or a range of wavelengths between about 10 nm and about 400 nm. Thus, device 2 is capable of emitting UV light at a germicidal wavelength of about 265 nm to about 280 nm as well. The device 2 may emit the UV light at a distance of up to 18 feet or more. This distance may be ever further if there is significant increase in output power to the UV light emitting source 1. The device 2 is activated by a dynamic (variable) logic process to ensure that the device is inactive when the device detects a presence by the detector 4. Activation is by control module 3, which is controlled by the dynamic (variable) logic process and associated algorithm(s) described above In further examples, UV light emitting sources that resembled light emitting diodes but embedded in UV light transmissive material were tested. Initial light transmissive materials included glass and treated polymethyl methacrylate (PMMA). With these materials, 30% of microbes (bacteria, algae, and parasites in contaminated water) were killed after 5 minutes of UV light exposure. Kill rates were significantly higher when exposure times were increased to at least or greater than 30 minutes.

When UV light was projected to a ultraviolet transmissive PMMA, the internal structure of various microbes darkened within 30 to 45 seconds and all (100%) of the bacteria as well as parasitic organisms were killed within three minutes, at which time greater than 90% of the organisms showed visible cell wall rupture. Algae were killed at or after 30 minutes exposure with similar cell wall disruption.

Figure 11:
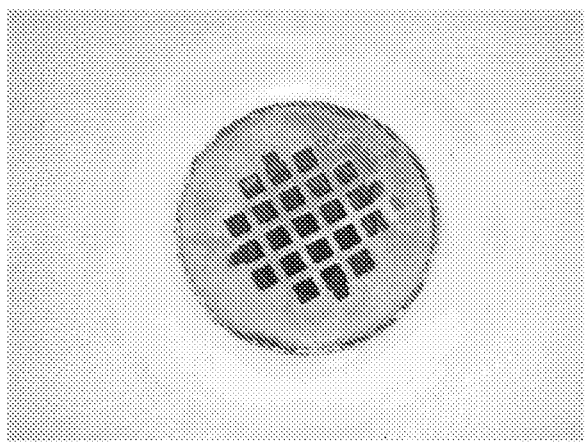
FIG. 11 depicts a drain with mold and fungus before activation of a device described herein.
Figure 12:
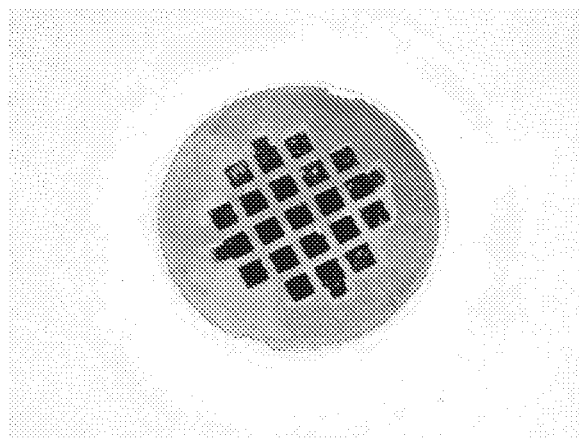
FIG. 12 depicts the drain of FIG. 11 without mold and fungus after activation with a device described herein.

A handheld device positioned at a distance of about 1 to 3 inches away was tested on fungal and mold colonies residing on a household surface, such as in showers and round drains (FIG. 11) Greater than 95% of the fungus and mold were killed with exposures of 15 minutes and 30 minutes, as shown in FIG. 12.

In the claims, the word "comprising" does not exclude other elements or steps, and the indefinite article "a" or "an" does not exclude a plurality. The mere fact that certain measures are recited in mutually different dependent claims does not indicate that a combination of these measured cannot be used to its advantage.

The foregoing description includes examples embodying, at least in part, certain teachings of the invention. The invention, as defined by the appended claims, is not limited to the described embodiments. Alterations and modifications to the disclosed embodiments may be made without departing from the invention. The meaning of the terms used in this specification are, unless expressly stated otherwise, intended to have ordinary and customary meaning and are not intended to be limited to the details of the illustrated structures or the disclosed embodiments. Although the foregoing description of embodiments have shown, described and pointed out certain novel features of the invention, it will be understood that various omissions, substitutions, and changes in the form of the detail as illustrated as well as the uses thereof, may be made by those skilled in the art, without departing from the scope of the invention. Particularly, it will be appreciated that the one or more embodiments may manifest itself in other configurations as appropriate for the end use of the material made thereby.

What is claimed is:

1. A fluid sanitizing system comprising:
   a containment vessel having an inlet, an outlet and an interior area for holding the fluid therein;
   a conduit disposed in the interior area and fluidly coupled to the inlet at a first end of the conduit and having an opening at a second and opposite end of the conduit, the opening exposed to the interior area to direct fluid through the inlet into the interior area such that the fluid within the interior area has the same direction of a rotational flow as the fluid within the conduit, the conduit having a plurality of coils between the first and second ends, the coils having a coil diameter, the coil diameter extending a distance less than a radius of the containment vessel;
   at least one photonic source disposed within the vessel, the at least one photonic source generating and emitting photonic energy in at least one wavelength;
   a heat sealed lens formed of a fluoropolymer material and surrounding the at least one photonic source such that the at least one photonic source and the fluoropolymer material include all components for generating and emitting photonic energy when the photonic source is activated such that it is an operable source; and
   wherein the heat sealed lens forms a submersible layer around at least a portion of the photonic source such that a portion of the operable source is waterproof, and the operable source and the conduit are positioned within the interior area to be fully submerged within the fluid such that at least a portion of the fluid within the interior area comes into direct contact with the operable source and is exposed to photonic energy so as to produce a sanitizing effect upon the fluid.

2. The device of claim 1, wherein the at least one photonic source is coupled with the lens such that the photonic energy emitting from the at least one photonic source transmits through and projects beyond the fluoropolymer material, wherein the lens propagates photons in an omnidirectional pattern simultaneously throughout the entirety of the coupled lens.

3. The device of claim 1, wherein the conduit is formed of a fluoropolymer tube for receiving fluid therein to be exposed to sanitizing photonic energy.

4. The device of claim 3, wherein the fluoropolymer tube is coiled.

5. The device of claim 1, wherein the fluoropolymer material comprises fluorinated ethylene propylene (FEP).

6. The device of claim 1, wherein the fluoropolymer material comprises ethylene tetrafluoroethylene (ETFE).

7. The device of claim 1, wherein the fluoropolymer material comprises perfluoroalkoxy alkanes (PFA).

8. The device of claim 1, wherein the lens is resistant to and does not materially degrade or become damaged from the photonic energy.

9. The device of claim 1, wherein the photonic source is a bulb.

10. The device of claim 1, wherein the photonic source is a light emitting diode.

11. The device of claim 1, wherein the photonic source is a laser diode.

12. The device of claim 1, wherein the lens is resistant to and does not materially degrade or become damaged from exposure to heat generated by the photonic source.

13. The device of claim 1, wherein there is no gap between the lens and the photonic source.

14. The device of claim 1, wherein the at least one photonic source is mounted to a light bar, such that the light bar is an inclusive part of the operable source.

15. The device of claim 14, wherein the at least one photonic source is mounted to a light bar, the at least one photonic source may be is configured to generate different wavelengths upon at least one and up to 6 different sides.

16. The device of claim 1, wherein embedding between the lens and the photonic source is such that the photonic source and lens are not divisible as separate functional components.

17. The device of claim 1, wherein the photonic source embedded within and underneath the outer surface of the lens allows the device to be protected from and impervious to one or more of damage and tampering.

18. The device of claim 1, wherein the lens is abraded.

19. The device of claim 1, wherein the device further comprises a shield such that the photons emitting from the at least one photonic source are focused and projected in a predetermined direction.

20. The device of claim 19, wherein a shield is embedded within and underneath the outer surface of the lens.

21. The device of claim 20, wherein the shield is positioned to focus and project the photons in a unilateral direction to an area beyond the surface of the lens.

22. The device of claim 14, wherein the at least one photonic source is mounted to a light bar, the light bar having a hexagonal cross section.

23. The device of claim 1, wherein the vessel further includes:
a top wall and an opposed bottom wall disposed opposite the top wall; and
wherein the outlet of the conduit is positioned in the vessel at a position closer to the bottom than the top wall.

24. The device of claim 1, wherein a volume of the interior area and a size of the conduit facilitate an exposure of the fluid to the UV source greater than ten seconds from entry to exit of the fluid within the interior area.

25. The device of claim 1, wherein the shape and position of the conduit and the shape of the interior area induce a vortex upon the fluids passing through and exiting the conduit such that the vortex is further induced upon the fluid within the vessel prior to exiting the vessel.

26. A fluid sanitizing system comprising:
a containment vessel having an inlet, an outlet and an interior area for holding the fluid therein;
a conduit having a plurality of coils disposed in the interior area and fluidly coupled to the inlet at a first end of the conduit and having an opening at a second and opposite end of the conduit, the plurality of coils having a coil diameter, the opening positioned adjacent the bottom wall for directing fluid from the inlet into the interior area adjacent the bottom wall such that the fluid within the interior area has the same direction of a rotational flow as the fluid within the conduit, wherein the coil diameter extends a length less than a radius of the containment vessel;
at least one photonic source generating and emitting photonic energy in at least one wavelength and a lens formed of a fluoropolymer material heat shrunk around the at least one photonic source such that the at least one photonic source and the fluoropolymer material include all components for generating and emitting photonic energy when the photonic source is activated such that it is an operable source; and
the operable source positioned within the interior area such that at least a portion of the fluid inside the interior area comes into direct contact with the operable source and is sanitized in response to exposure to the photonic energy.

27. The device of claim 26, wherein a volume of the interior area and a size of the conduit facilitate an exposure of the fluid to the UV source greater than ten seconds from entry to exit of the fluid within the interior area.

* * * * *